(12) United States Patent
Tweed et al.

(10) Patent No.: US 7,601,123 B2
(45) Date of Patent: Oct. 13, 2009

(54) NON-INVASIVE BLOOD PRESSURE MONITORING DEVICE AND METHODS

(75) Inventors: David Tweed, Melbourne, FL (US);
Patrick G. Phillips, Lincoln, MA (US);
Paul Epstein, Tiburon, CA (US)

(73) Assignee: Eppcor, Inc., Lincoln, MA (US)

( * ) Notice: Subject to any disclaimer, the term of this patent is extended or adjusted under 35 U.S.C. 154(b) by 875 days.

(21) Appl. No.: 10/922,826

(22) Filed: Aug. 20, 2004

(65) Prior Publication Data

US 2005/0148885 A1 Jul. 7, 2005

Related U.S. Application Data

(60) Provisional application No. 60/497,438, filed on Aug. 22, 2003.

(51) Int. Cl.
*A61B 5/02* (2006.01)
(52) U.S. Cl. .............. 600/490; 600/481; 600/485; 600/493; 600/499
(58) Field of Classification Search .......... 600/480, 600/481, 485, 490–503
See application file for complete search history.

(56) References Cited

U.S. PATENT DOCUMENTS

| | | | |
|---|---|---|---|
| 3,412,729 A | 11/1968 | Smith | |
| 4,524,777 A * | 6/1985 | Kisioka et al. | 600/490 |
| 4,821,734 A | 4/1989 | Koshino | |
| 4,846,189 A | 7/1989 | Sun | |
| 5,237,997 A | 8/1993 | Greubel et al. | |
| 5,269,310 A | 12/1993 | Jones et al. | |
| 5,368,039 A | 11/1994 | Moses | |
| 5,423,322 A * | 6/1995 | Clark et al. | 600/485 |
| 5,830,131 A * | 11/1998 | Caro et al. | 600/300 |
| 6,132,383 A * | 10/2000 | Chesney et al. | 600/502 |
| 6,280,390 B1 * | 8/2001 | Akselrod et al. | 600/485 |
| 2003/0092999 A1 * | 5/2003 | Goto et al. | 600/485 |
| 2005/0131308 A1 * | 6/2005 | Chio et al. | 600/490 |
| 2006/0074322 A1 * | 4/2006 | Nitzan | 600/485 |
| 2006/0116588 A1 * | 6/2006 | Archibald et al. | 600/494 |

\* cited by examiner

*Primary Examiner*—Robert L Nasser
*Assistant Examiner*—Karen E Toth
(74) *Attorney, Agent, or Firm*—Wilmer Cutler Pickering Hale and Dorr LLP

(57) ABSTRACT

The apparatus and methods of the present invention provide a non-invasive measurement of blood pressure with a frequency that approximates a continuous measurement. Blood pressure measurement provides information that is both clinically and diagnostically significant. In accordance with an aspect of the present invention, a method for providing a non-invasive measurement of blood pressure, includes obtaining a first input signal and a second input signal indicative of systolic blood pressure and diastolic blood pressure, respectively; tracking a signal indicative of pulse pressure; continuously measuring a third signal indicative of mean blood pressure; and processing the signals to obtain a measurement indicative of systolic and diastolic blood pressure, wherein at least a portion of the measurement indicative of systolic and diastolic blood pressure is continuous. The second input signal indicative of diastolic blood pressure is analyzed to identify a maximum amplitude of the signal, the maximum amplitude being indicative of the diastolic blood pressure measurement.

18 Claims, 31 Drawing Sheets

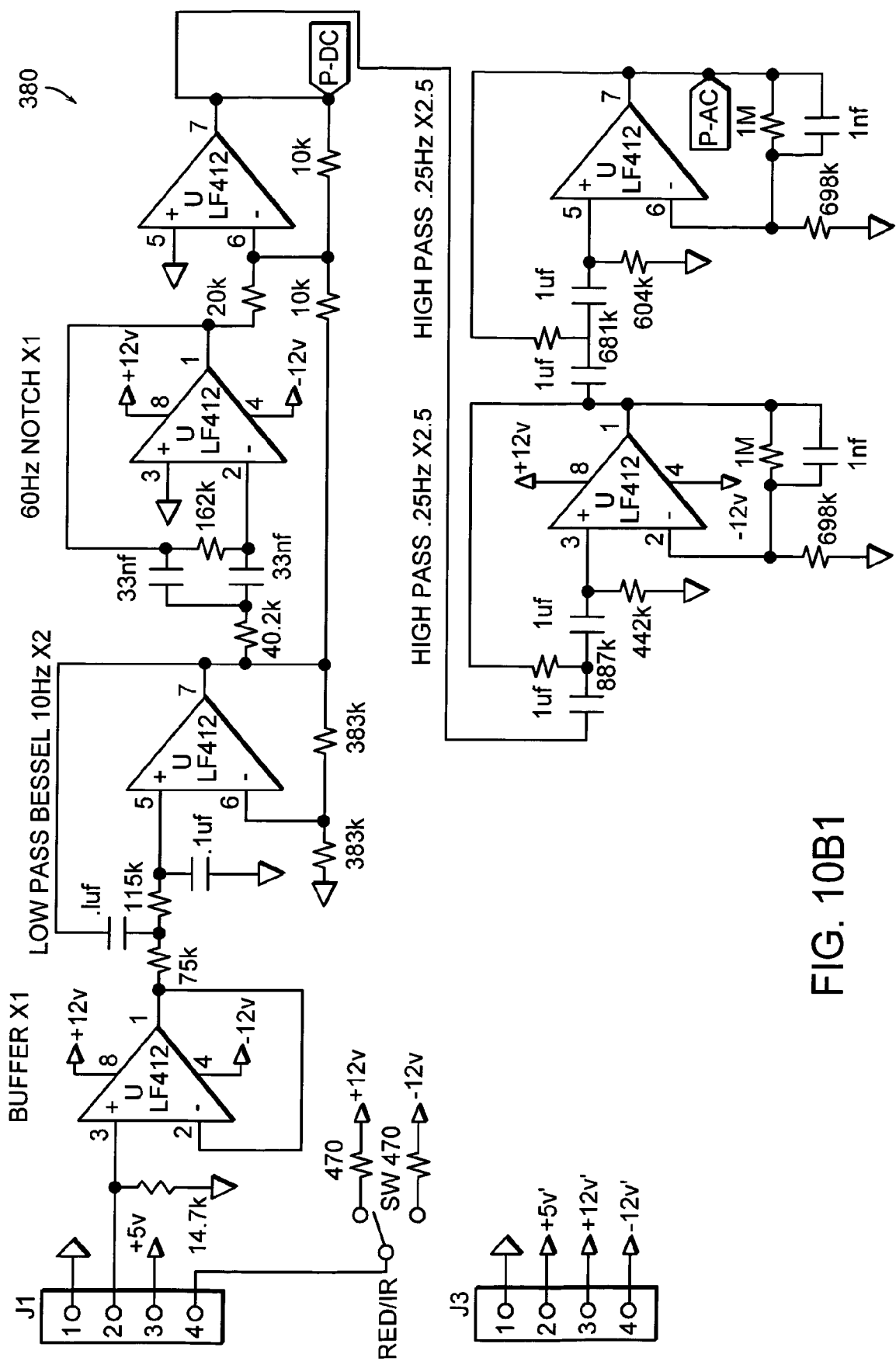
FIG. 10B1

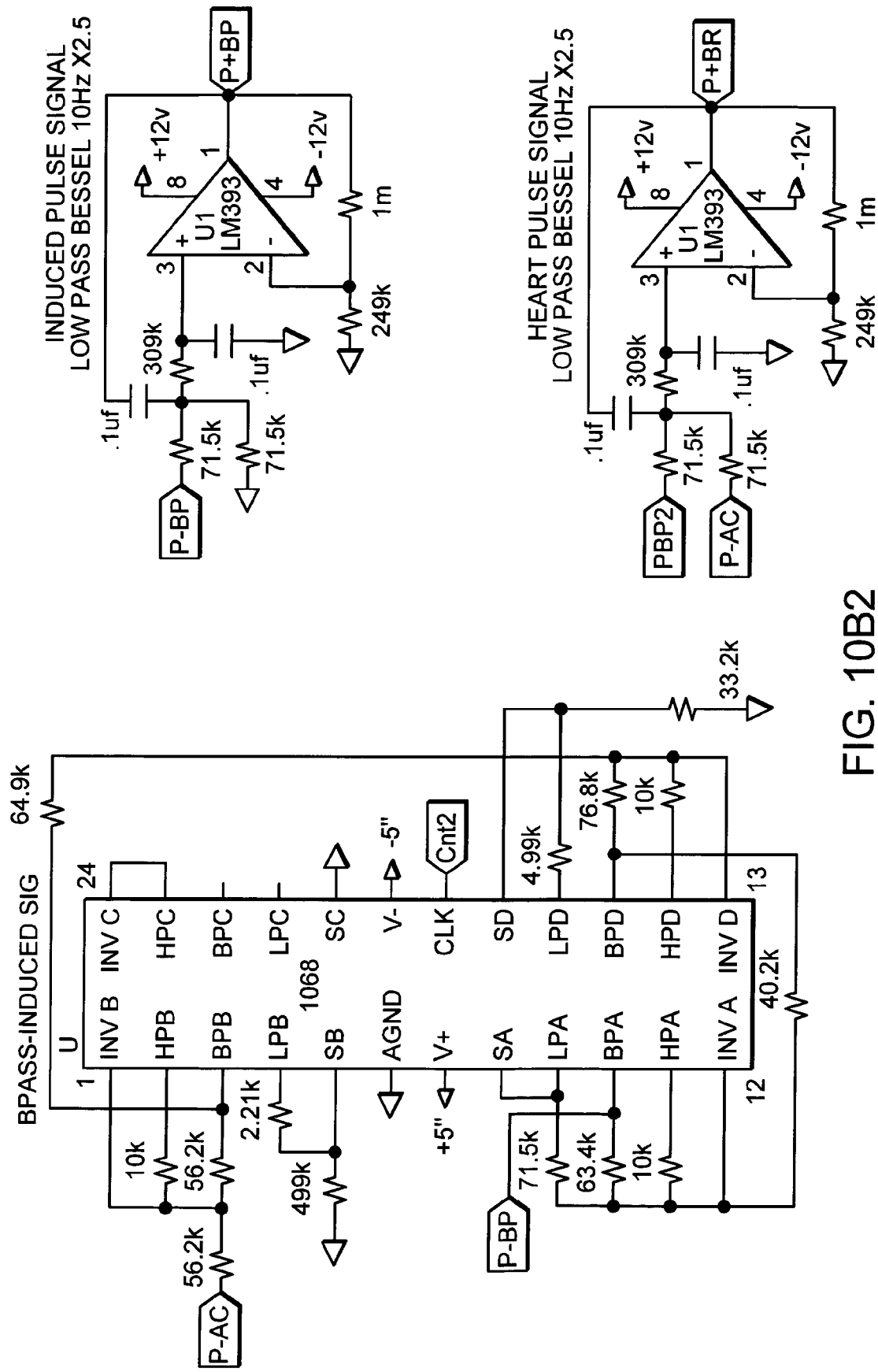
FIG. 10B2

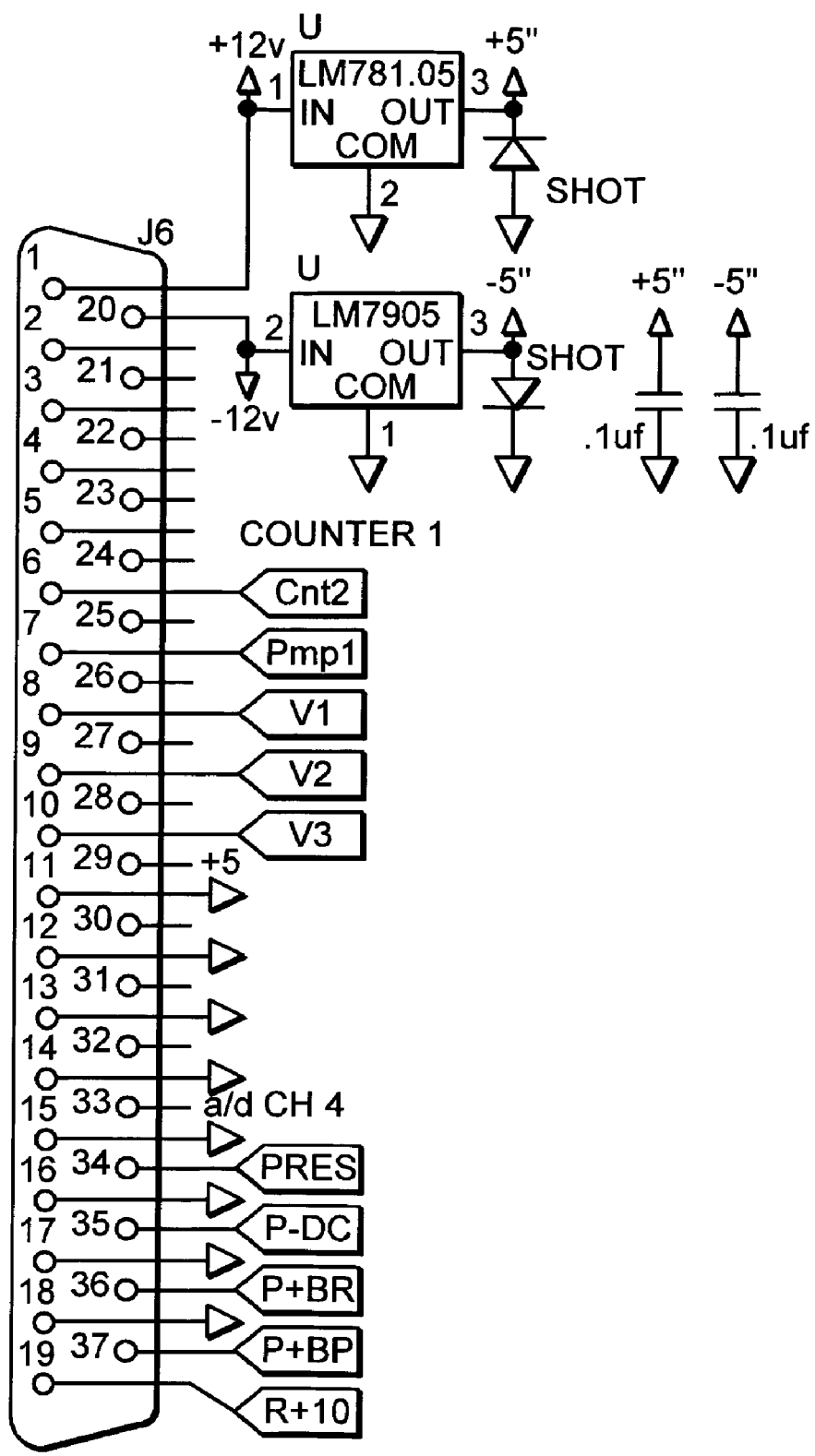
FIG. 10B3-1

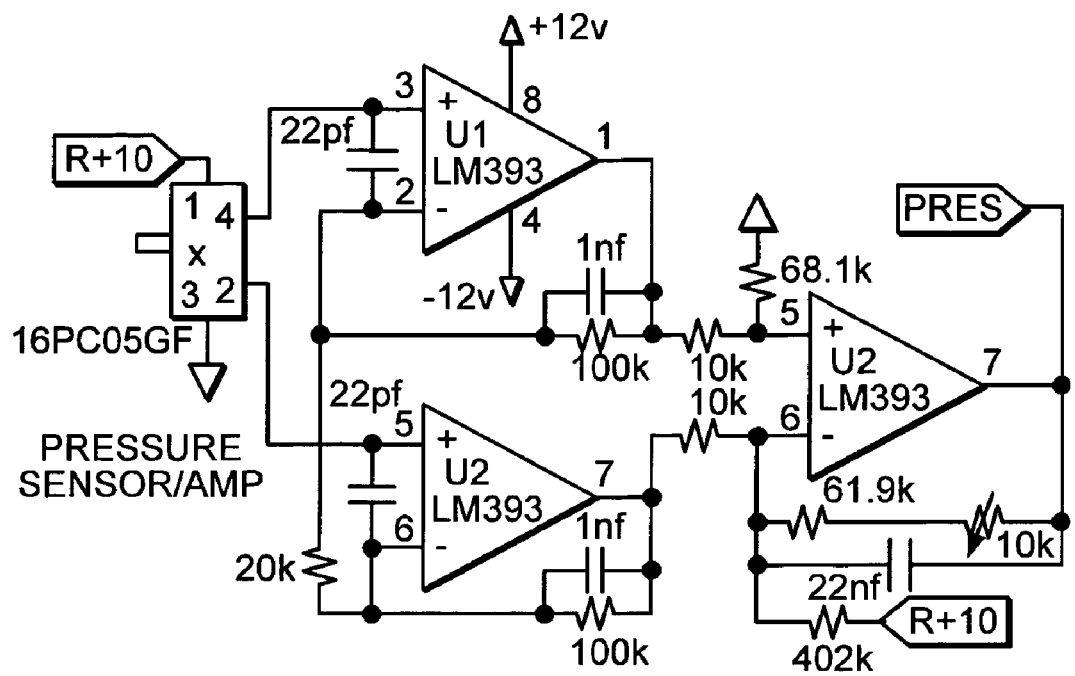
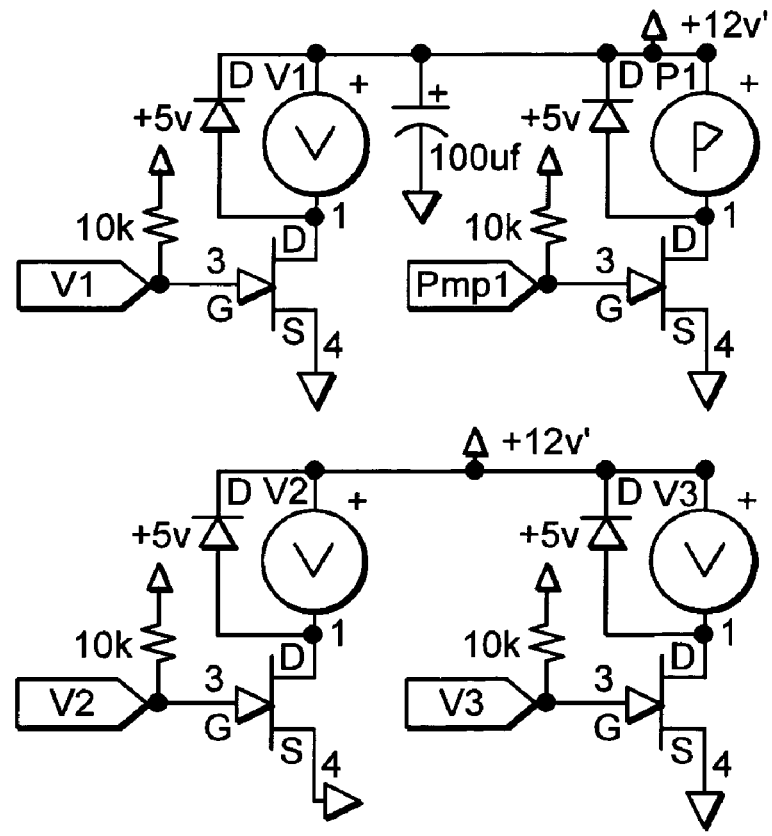
FIG. 10B3-2

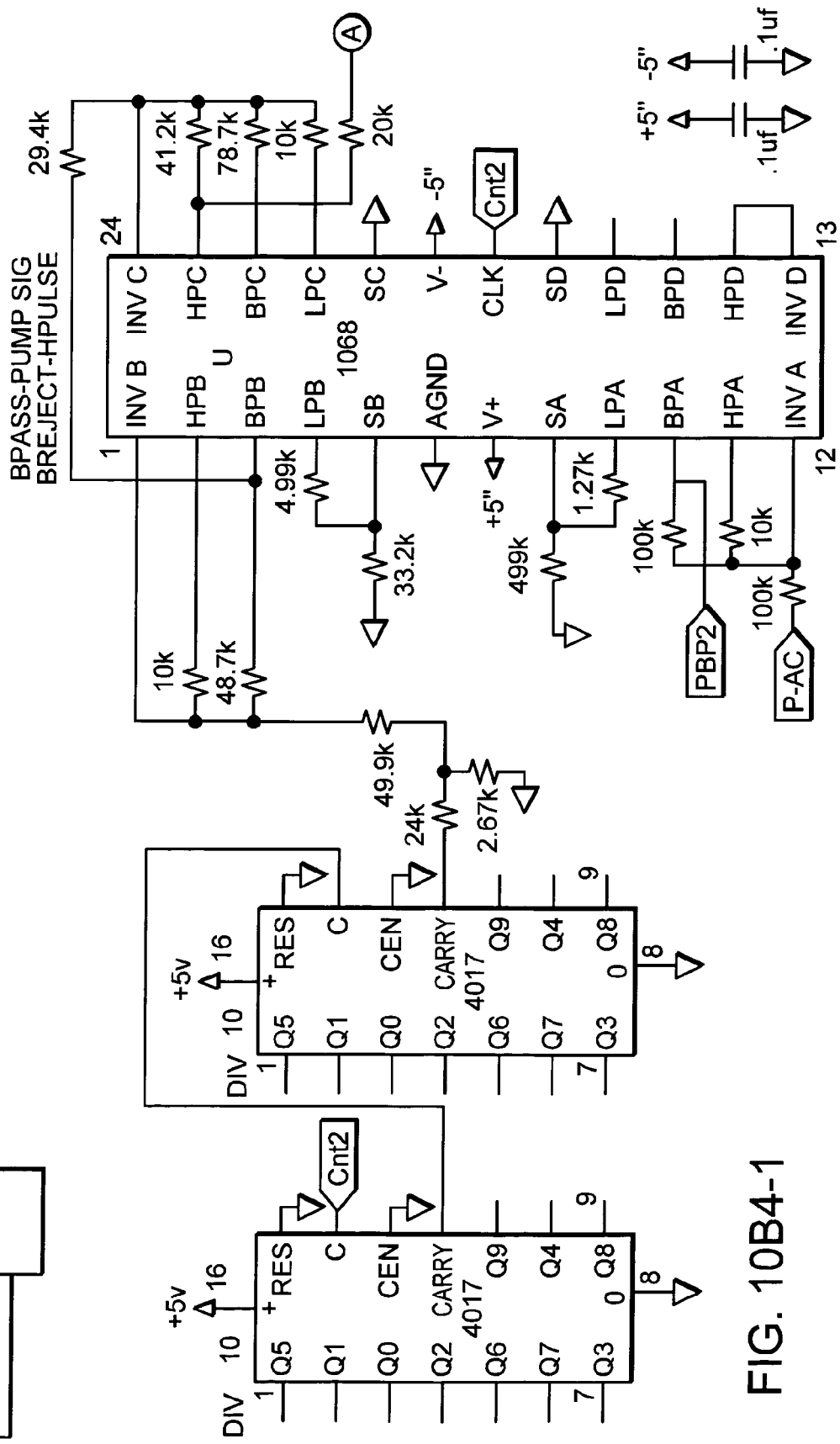

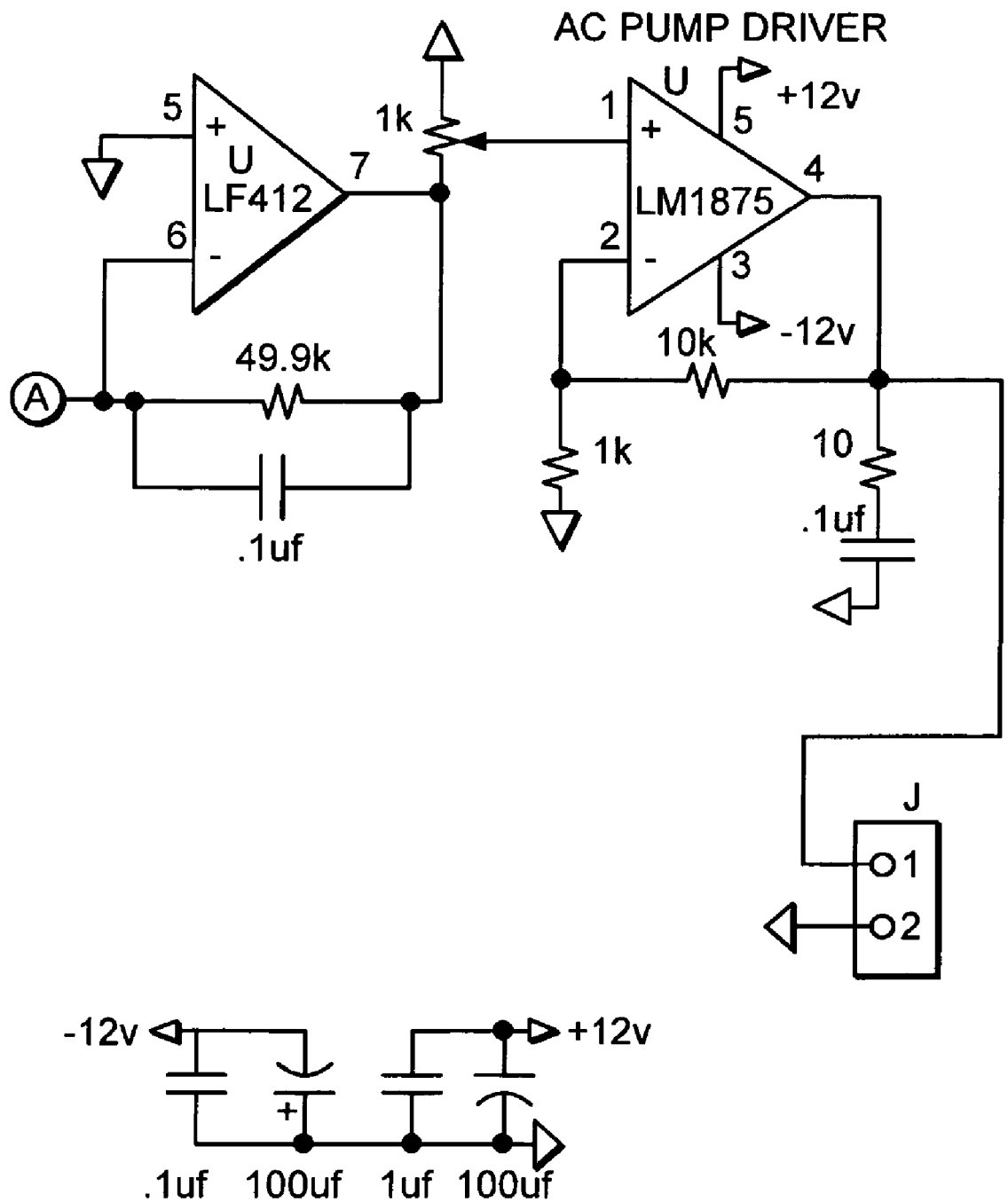
FIG. 10B4-2

NON-INVASIVE BLOOD PRESSURE MONITORING DEVICE AND METHODS

CROSS-REFERENCE TO RELATED APPLICATIONS

This application claims benefit to U.S. Provisional Patent Application Ser. No. 60/497,438 filed on Aug. 22, 2003, the entire contents of which is incorporated herein by reference.

TECHNICAL FIELD

The present invention relates generally to a device for the non-invasive monitoring of blood pressure. More particularly, the present invention provides an apparatus and methods for monitoring blood pressure non-invasively.

BACKGROUND

Blood pressure is a physiologic parameter that is often measured to gain an understanding about the condition of a person's cardiovascular system and overall health. Arterial blood pressure, referred to simply as blood pressure, is caused by the pumping action of the left ventricle of the heart and the resistance to flow caused by the vascular system. When the heart beats or "pumps", blood is forced through the arteries to the capillaries. Blood pressure is typically characterized by two readings, the systolic and diastolic pressures. The systolic pressure is the pressure as the heart contracts and is the higher of the two pressures. The diastolic pressure is the pressure when the heart relaxes and fills with blood in preparation for another contraction.

In a typical measurement of blood pressure a cuff is secured around a patient's limb and is inflated to a sufficiently high pressure to cut off arterial blood flow beneath the cuff and then the cuff is gradually deflated to allow the artery to slowly open. As the cuff is deflated, blood is able to pass through the blood vessel beneath the cuff. As the blood is able to pass through, sounds, known as Korotkoff sounds, are created and form biological signals indicative of blood pressure. These sounds can be detected by a trained clinician using a stethoscope to determine a person's blood pressure. This is known as an occlusive measurement because the artery is occluded (pressed shut) for a brief period of time during the measurement.

An alternative non-invasive way to determine blood pressure on the basis of sounds is to detect the Korotkoff sounds by a transducer. When the blood pressure sounds are detected by a transducer they are converted into an electrical signal that is processed to determine the systolic and diastolic pressure. Other types of non-invasive techniques to determine blood pressure are known. For example, an oscillometric technique measures the pressure change in a cuff induced by flowing blood and converts the pressure change to an electrical signal which is used as the basis for determining blood pressure. Another procedure involves using multiple transducers to detect the occurrence of heart pulses at different locations along the artery. In this example mean blood pressure is determined by the pulse propagation time between the transducers.

Blood pressure can be accurately determined by using a catheter that is fitted with a pressure transducer and inserting the catheter into an artery. The pressure that is measured is direct and accurate. The measurement is also continuous. However, this technique has the disadvantage of being invasive. That is, to obtain blood pressure reading this way, a patient must have a puncture through the skin in order to deliver the catheter into the blood vessel.

Often it is clinically desirable to measure blood pressure during critical care periods of a patient. For example, during surgery it is desirable to know a persons blood pressure so that the anesthesiologist can monitor the patients. It is advantageous that the measurement be continuous because of the risks to the patient during surgery. An occlusive measurement cannot be repeated with the frequency that may be desired in the operating room. Additionally, patient monitoring before and after surgery typically includes monitoring the blood pressure. Currently, there is no single reliable non-invasive measurement device or technique that provides a clinician with continual blood pressure information that is desired.

SUMMARY OF THE INVENTION

The apparatus and methods of the present invention provide a non-invasive measurement of blood pressure with a frequency that approximates a continuous measurement. Blood pressure measurement provides information that is both clinically and diagnostically significant.

In accordance with an aspect of the present invention, a method for providing a non-invasive measurement of blood pressure, includes obtaining a first input signal and a second input signal indicative of occlusive measurements of systolic blood pressure and diastolic blood pressure, respectively; tracking a signal indicative of pulse pressure; continuously measuring a third signal indicative of mean blood pressure; and processing the signals to obtain a measurement indicative of systolic and diastolic blood pressure, wherein at least a portion of the measurement indicative of systolic and diastolic blood pressure is continuous. The second input signal indicative of diastolic blood pressure is analyzed to identify a maximum amplitude of the signal, the maximum amplitude being indicative of the diastolic blood pressure measurement.

The input signals are obtained from a photo-plethysmograph which includes a light source and a detector. The light source is a light emitting diode, a laser or an incandescent lamp. The detector is one of a photocell or a photo-resistive device.

The tracking of a signal indicative of pulse pressure, wherein pulse pressure is characterized as the difference between a systolic pressure measurement and a diastolic pressure measurement, includes inducing a pulse signal into a region of interest, and obtaining a resultant signal indicative of a combination of the induced pulse signal and a heart pulse signal. The processing of the resultant signal further comprises amplifying the resultant signal, separating the induced pulse signal from the heart pulse signal and calculating the pulse pressure from the relative amplitudes of the induced pulse signal and the heart pulse signal. The method further includes minimizing a venous response to the induced pulse signal by either selecting an appropriate frequency for the induced pulse signal and/or applying a constant pressure to the region of interest. Further, the method comprises continuously monitoring a voltage signal of a photo-plethysmograph and an amplitude signal of an induced pulse signal to derive a continuous measure of mean blood pressure. The amplitude of the induced pulse signal is proportional to a compliance characteristic of an arterial vasculature. The method further includes calculating a function of the voltage signal and the amplitude signal, wherein the function is proportional to the mean blood pressure. In an embodiment, the function is a geometric mean of the voltage signal and the amplitude signal.

The method further includes determining a continuous measurement indicative of systolic blood pressure from the relationship defined by mean blood pressure added to a fraction of the pulse pressure. In an embodiment, the fraction of the pulse pressure is two-thirds. The method further comprises determining a continuous measurement indicative of diastolic blood pressure from the relationship governed by a fraction of the pulse pressure subtracted from mean blood pressure. In an embodiment, the fraction of pulse pressure is one-third. The method further includes performing a plurality of processing cycles or iterations upon obtaining a new first input signal and new second input signal or changes to different hemodynamic parameters or at a predetermine frequency.

In accordance with another aspect, a method for monitoring a continuous blood pressure measurement of a subject such as a critical care patient, comprises the steps of: calibrating a signal indicative of a mean pressure tracking parameter; measuring continuously and tracking a signal indicative of pulse pressure; calculating a continuous measurement indicative of mean blood pressure; and processing at least the continuous measurement indicative of mean blood pressure to obtain measurements indicative of continuous systolic blood pressure and continuous diastolic blood pressure. The method further includes obtaining a plurality of occlusive measurements indicative of blood pressure. The step of obtaining a plurality of occlusive measurements includes obtaining a first input signal indicative of a systolic blood pressure and second input signal indicative of diastolic blood pressure, and wherein the second input signal indicative of diastolic blood pressure comprises analyzing the second input signal to identify a maximum amplitude of the second input signal, the maximum amplitude being indicative of the diastolic blood pressure measurement. The first input signal and the second input signal are obtained from a photo-plethysmograph.

In accordance with another aspect of the present invention, a system for providing a continuous, non-invasive measurement of blood pressure, includes a sensor module to obtain a plurality of physiological signals indicative of blood pressure; and a control module in communication with the sensor module for data collection and processing, the control module having a processor to process the plurality of physiological signals to provide a continuous measurement indicative of blood pressure. The sensor module comprises a housing defining a compartment closed at a distal end and open at a proximal end for receiving a body part into the proximal end; a first membrane defining a first chamber containing a pressurized fluid to apply a static pressure field to the body part when received within the housing; a second membrane defining a second chamber; and at least one sensor in at least one of said first and second chamber for sensing changes in the body part. At least one sensor is a pressure sensor for sensing the pressure of a region of interest of the body part, and wherein at least one sensor is a photo-plethysmograph having a light source and an optical detector. The light source is one of a light emitting diode, a laser or an incandescent lamp while the optical detector is one of a photocell or a photo-resistive device. The sensor is located on an integrated circuit board.

The processor in the control module further comprises at least one of analog processing circuitry and digital processing circuitry. The analog processing circuitry provides at least one of a signal indicative of an induced pulse signal, a heart pulse signal, DC photocell signal, induced drive signal to an AC pressure pump, pressure signal to an analog to digital converter and a drive signal to a light source. The digital processing circuitry provides at least one of signal to a filter clock, graphics display, user interface, a pump, a plurality of valves and a power amplifier.

The control module includes a display unit for displaying the plurality of physiological signals indicative of blood pressure. The display unit may be integral with the control module or be a separate display monitor in communication with the control module. The plurality of physiological signals comprises at least one of pulse pressure, mean blood pressure, pulse waveform, alarm limits, diastolic blood pressure for a period of time and systolic blood pressure for a period of time. The control module further comprising a plurality of user interfaces to select different parameters such as time and alarm limits.

In accordance with another aspect of the present invention, a portable apparatus for monitoring non-invasively, blood pressure measurements of a patient, comprises a housing defining a compartment closed at one end and open at an opposite end for receiving a distal part of a body part, the housing having at least one sensor for measuring a signal indicative of blood pressure; a pump to pressurize at least one chamber in said housing; and a processing device in communication with the housing and pump to process the at least one signal to provide at least one signal indicative of blood pressure, wherein at least a portion of said signal is provided continuously. The housing comprises a first membrane defining a first chamber containing a pressurized fluid to apply a static pressure field to the body part when received within the housing; a second membrane defining a second chamber; and at least one sensor in at least one of said first and second chamber for sensing changes in the body part. At least one sensor is a pressure sensor for sensing the pressure of a region of interest of the body part. The sensor is a photo-plethysmograph. The portable apparatus weighs approximately 11 pounds.

In accordance with another aspect, a method for providing a non-invasive measurement of blood pressure, comprises obtaining an input signal indicative of diastolic blood pressure from an occlusive measurement; and analyzing the input signal indicative of diastolic blood pressure comprises analyzing the second input signal to identify a maximum amplitude of the signal, the maximum amplitude being indicative of the diastolic blood pressure measurement. The method further comprises: obtaining a first input signal and a second input signal indicative of occlusive measurements of systolic blood pressure and diastolic blood pressure, respectively; continuously measuring a third signal indicative of mean blood pressure; and processing said signals to obtain a continuous measurement indicative of systolic and diastolic blood pressure. The first input signal and the second input signal are obtained from a photo-plethysmograph, wherein the photo-plethysmograph comprises a light source and a detector.

In accordance with another aspect of the present invention, a method of providing a continuous, non-invasive measurement of blood pressure, includes tracking a signal indicative of pulse pressure, pulse pressure characterized as the difference between a systolic pressure measurement and a diastolic pressure measurement, comprising: inducing a pulse signal into a region of interest, and obtaining a resultant signal indicative of a combination of the induced pulse signal and a heart pulse signal. The processing of the resultant signal further includes amplifying the resultant signal, separating the induced pulse signal from the heart pulse signal and calculating the pulse pressure from the relative amplitudes of the induced pulse signal and the heart pulse signal. The method includes minimizing a venous response to the induced pulse signal by selecting an appropriate frequency for the induced pulse signal and/or applying a constant pressure to the region of interest. The method further comprises: obtaining a first input signal and a second input signal indicative of occlusive measurements of systolic blood pressure and diastolic blood pressure, respectively; continuously measuring a third signal indicative of mean blood pressure; and processing said signals to obtain a continuous measurement indicative of systolic and diastolic blood pressure.

Another aspect of the present invention includes a method for non-invasively monitoring blood pressure continuously comprising: measuring mean blood pressure by continuously monitoring a voltage signal of a photo-plethysmograph and an amplitude signal of an induced pulse signal. The amplitude of the induced pulse signal is proportional to a compliance characteristic of an arterial vasculature. The method further comprises: calculating a function of the voltage signal and the amplitude signal, wherein the function is proportional to the mean blood pressure. The function is a geometric mean of the voltage signal and the amplitude signal. The method further includes determining a continuous measurement indicative of systolic blood pressure from the relationship defined by mean blood pressure added to a fraction of pulse pressure. The fraction of pulse pressure is two-thirds.

The method further includes determining a continuous measurement indicative of diastolic blood pressure from the relationship governed by a fraction of pulse pressure subtracted from mean blood pressure, wherein the fraction is one-third in an embodiment. The method includes the steps of obtaining a plurality of occlusive measurements indicative of blood pressure; calibrating a signal indicative of a mean pressure tracking parameter; and measuring continuously and tracking a signal indicative of pulse pressure.

Another aspect of the present invention includes a sensor module for providing measurements indicative of blood pressure, comprising operating in a first mode for providing occlusive measurements indicative of diastolic blood pressure and systolic blood pressure, and operating in a second mode for continuously providing signals indicative of blood pressure. The sensor module further comprises a control module in communication with the sensor module for data collection and processing.

The foregoing and other features and advantages of the non-invasive blood pressure monitoring device and methods will be apparent from the following more particular description of the embodiments of the invention, as illustrated in the accompanying drawings in which like reference characters refer to the same parts throughout the different views. The drawings are not necessarily to scale, emphasis instead being placed upon illustrating the principles of the invention.

BRIEF DESCRIPTION OF THE DRAWINGS

FIGS. 10B1-10B4 are circuit diagrams illustrating the circuit components of an analog signal processor of an embodiment of the blood pressure monitoring device;

DETAILED DESCRIPTION

Figure 1:
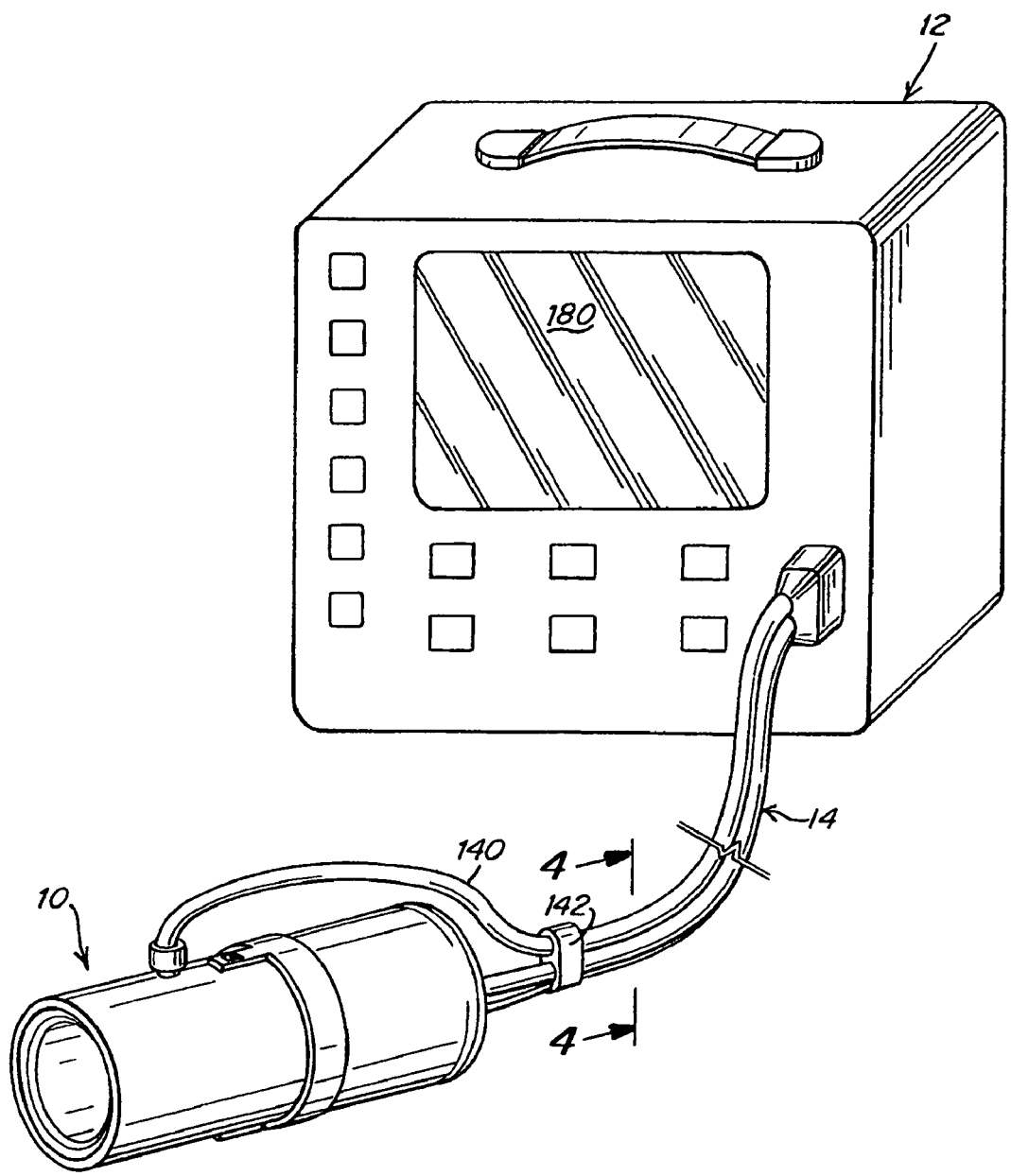
FIG. 1 is a schematic representation of a non-invasive blood pressure monitor including the control module and the sensor module according to one embodiment of the invention.

With reference to FIG. 1, an embodiment of the present invention provides a blood pressure measurement device and methods that include a sensor module 10 and a control module 12. The sensor module is adapted to detect signals related to a person's blood pressure which are transferred to the control module by a conduit 14. The control module processes the information and, according to an algorithm or sequence of executable instructions, computes the systolic and diastolic pressure of a patient.

The device and methods are adapted to provide an occlusive blood pressure measurement as a base line and then using certain parameters of the blood, for example, mean blood pressure and pulse pressure, a blood pressure measurement is continually determined. The methods are directed at providing continuous information indicative of blood pressure. The blood pressure information is provided at least several times a minute and is considered clinically to approximate a continuous measurement. In an embodiment the information can be updated at a frequency that is more or less than several times a minute and yet approximate a continuous measurement. After a predetermined period of time or other change in condition, another occlusive measurement may be taken to determine a new baseline measurement.

The measurements in the sensor module are obtained by a photo-plethysmograph having a light source, for example, an LED (light emitting diode) and a photodetector, for example, a photocell (sensor). The LED and the sensor are disposed on opposite sides of a digit (finger), for example, by placing the LED on the fingernail side of the digit and a photocell sensor on the fingerprint or pad side of the digit. The measurements are based on the amount of light that passes through the digit. The embodiments of the invention are described with reference to an LED—photocell measurement technique. There are other ways of measuring the physiologic parameter information sought and the description of the particular sensor system is not intended to limit the scope of the invention. It should be noted that other light sources, for example, incandescent lamps, solid state lasers or other suitable lasers, and fiber optics to conduct light can be used as alternatives to the LED. Similarly, other photoresistive devices or any device responsive to light intensity can be used as an optical sensor. Additionally, the use of a finger (or other digit) is an illustration and is not intended to limit the scope of the invention in any way.

Figure 2:
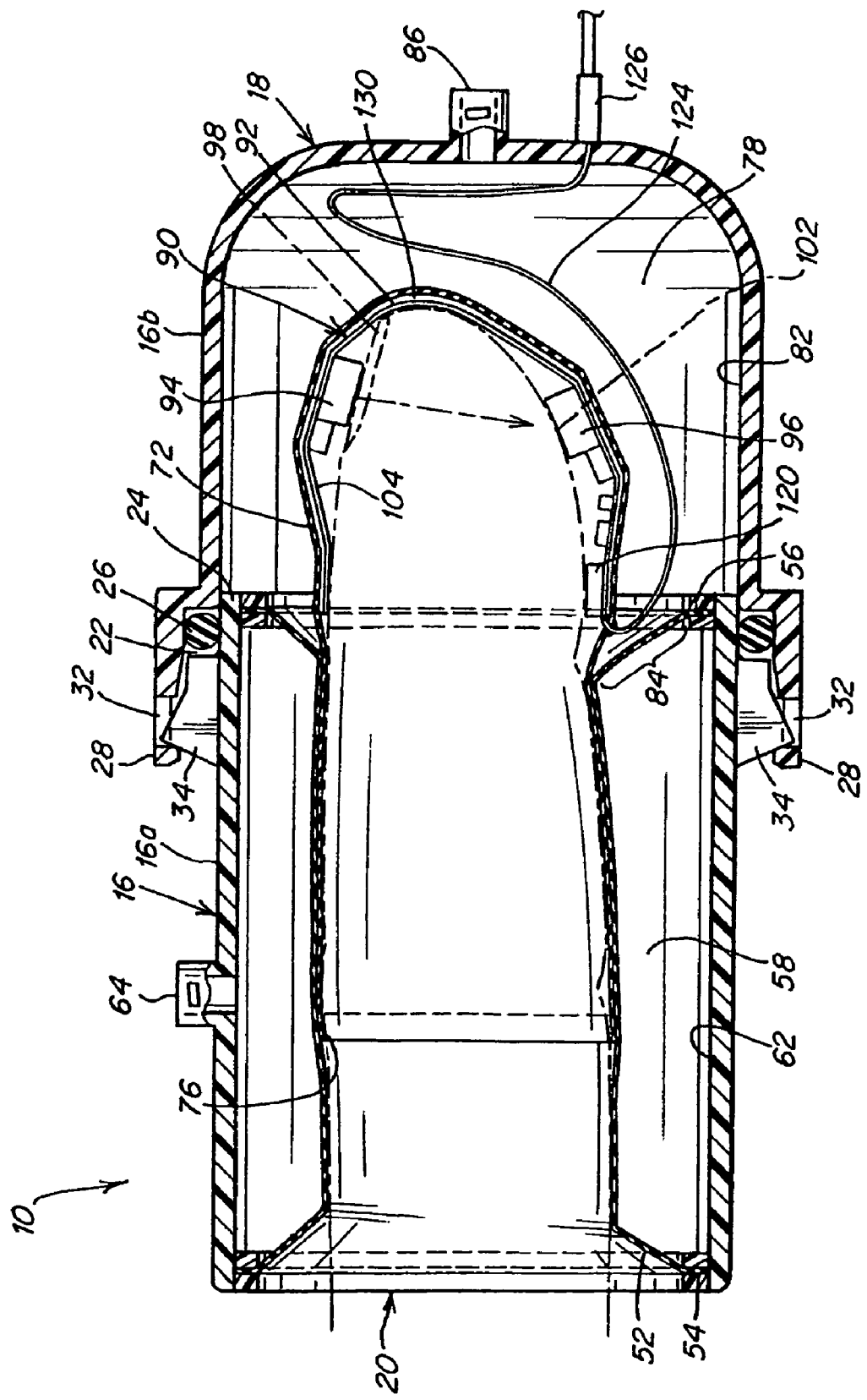
FIG. 2 is a longitudinal cross-section of the sensor module adapted for a finger.

With reference to FIGS. 1 and 2, the sensor module 10 is a generally cylindrical rigid housing 16 that is closed on one end 18 and open on the other end 20. The housing may be formed of any generally rigid material such as metal or rigid plastic. Advantageously, the housing may be molded by any technique known to form material suitable to be used in a medical context. For example, the housing may be formed with acrylic (PMMA), nylon, polyethylene terephthalate (PET), or other plastic materials. The housing may be constructed in two pieces, a proximal piece 16a and a distal piece 16b. As used in this application the terms proximal and distal refer to the location of an element relative to a patient. So, for example, the proximal piece of the sensor housing would be nearer the patient and the distal piece of the sensor housing would be further away from the patient. The housing pieces may be of any configuration that, when joined, the housing with a closed end and an open end is formed.

A two-piece construction may be helpful to allow a clinician to check and secure the various components of the sensor module to a patient's finger. As shown schematically in FIG. 2, the pieces 16a and 16b are joined at about half the longitudinal distance of the housing. The pieces of the housing can be joined by a variety of securing devices. In the embodiment shown, the piece 16b has an open end that has a larger diameter on its open end 22 which is adapted to fit the end portion 24 of the cylindrical piece 16a. The larger diameter is sufficient to accommodate an O-ring 26 which is disposed at the joint between the pieces 16a and 16b. The O-ring provides a seal between the pieces and prevents fluid (air) from escaping the sensor module during the measurement procedure.

The two pieces 16a and 16b are secured to one another by a locking mechanism that includes generally flexible arms 28 that extend from the larger diameter portion 22. The flexible arms 28 have apertures 32 which are adapted to receive cooperating protrusions 34. The protrusions extend radially from the outer cylindrical surface of the piece 16a. The protrusions 34 are secured into the aperture 32 and lock the pieces 16a and 16b together. As illustrated in FIG. 2, the locking mechanism may have two flexible arms that cooperate with the protrusions. The locking mechanisms may be spaced at regular intervals along the circumference of the housing. Of course, one skilled in the art will recognize there are other locking mechanisms that would be equally effective at holding the two pieces together. Additionally, one skilled in the art will recognize that in alternative embodiments the housing need not be split at all. Alternatively, the housing may be split along the longitude of the housing to form cooperating semicircular cross-sectioned housing pieces which when secured together form the cylindrical sensor housing.

The diameter of the housing of the described embodiment is sized to be larger than a human finger. In an embodiment of the invention, the housing is adapted to have two inflatable bladders disposed inside. A first bladder, finger cuff 52 is attached to the housing at a proximal attachment location 54 and a distal attachment location 56. The proximal and distal attachment locations extend around the entire circumference of the housing. A variety of attachment techniques may be used to fix the bladder material to the housing such as glue or welding (whether heat or vibration). The finger cuff 52 forms a proximal air chamber 58 which is bounded by the inside surface 62 of the housing and the finger cuff. Thus a circumferential cuff is formed which is adapted to expand and surround a portion of a finger which is disposed in the housing. Typically, the finger cuff extends from between the first and second knuckle and the second and third knuckle. The cuff is air-tight and, when inflated, can occlude the blood flow through the finger.

The finger cuff bladder material may be constructed of a variety of suitable materials. For example, in an embodiment, the bladder is constructed of polyurethane or latex. Since latex has caused allergic reactions in some people, the preferred material is polyurethane. The housing includes a finger cuff fill port 64. The port may be molded into the housing or fixed to the housing in a subsequent fabrication operation. In one embodiment, the fill port includes a "quick connect" feature such a Luer Lock so that the assembly operation time may be minimized.

The second bladder is a finger sleeve 72. The sleeve 72 is adapted to receive a finger in the same manner that a finger would go into a glove. The finger sleeve 72 is attached to the housing at a proximal attachment location, which in the embodiment described, is the same as the proximal attachment location 54 for the finger cuff 52. The sleeve is intended to fit inside the finger cuff and extend beyond the distal end of the finger cuff. A finger should be able to fit comfortably inside the finger sleeve when the sleeve is uninflated. Like the finger cuff, the finger sleeve may be constructed of polyurethane or latex. The finger sleeve is attached to the finger cuff at an attachment ring 76. The attachment ring 76 is located between the distal and the proximal attachment locations and helps to absorb stresses that occur as a result of the bladders being inflated.

A distal air chamber 78 which envelops the distal part of the finger is formed by the finger sleeve and inside surface 82 of the housing. The finger cuff zone 84 is the boundary between the proximal air chamber and the distal air chamber. The distal air chamber 78 is filled with distal air chamber port 86. Similar to the proximal air chamber port, the distal air chamber port may have a Luer Lock to facilitate connection between the air line and the sensor housing. The air chambers may be separately filled and evacuated. The finger cuff 52 can be used to occlude blood flow in the finger and thus obtain an occlusive measurement of the blood pressure of a patient. Additionally, the finger cuff can be inflated when the finger sleeve is also inflated and thus prevent the finger from slipping out of the sensor housing due the pressure exerted on the end of the finger.

As an alternative to using the finger cuff to prevent the finger sleeve from rolling off the finger when it is inflated, the distal end of the finger sleeve may be attached to the distal wall of the housing. The attachment may be an attachment member that would be flexible and not elastic attached on one end to the finger sleeve and on the other end to the inside of the housing. The attachment member should be flexible to allow the finger sleeve to move as it is being inflated and non-elastic so that the finger sleeve does not roll. Pressure should not be applied to the finger by the attachment member as any pressure that is applied by the housing could skew a reading by the pressure sensor.

Figure 3A:
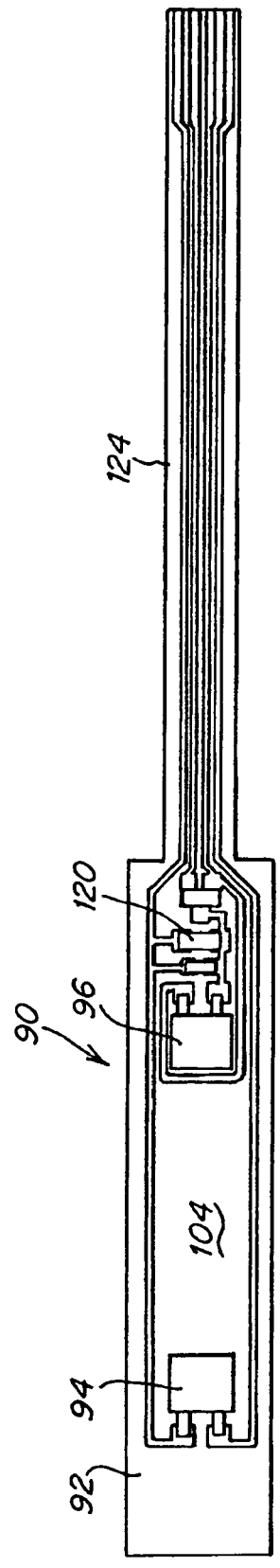
FIGS. 3A and 3B illustrate top and side views, respectively, of a circuit board layout of the sensor used in the sensor module.
Figure 3B:
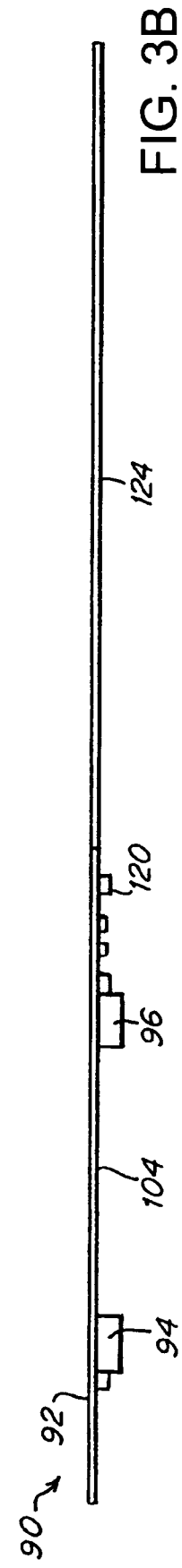

The sensor 90 uses light to determine the physiological parameters. As shown in the device in FIG. 2 and as a top view in FIG. 3A and side view in FIG. 3B, the sensor is built upon a flexible circuit board 92 that may be constructed of a polyimide such as Kapton. A light emitting diode (LED) 94 is attached to one end of the board 92. A photocell 96 is attached to the board 92 a distance away from the LED sufficient such that when the board is disposed on the tip of a finger, the LED 94 can be disposed on a finger nail 98 and the photocell can be disposed on the other side of the finger at the finger print pad 102 (as shown in FIG. 2). Thus, in the presently described embodiment, light from the LED travels through the finger and is received by the photocell. The amount of light that travels through the finger depends upon what is blocking the light. If the appropriate frequency of light is chosen, the light transmitted through the finger can vary depending on the amount of blood in the finger. LED's and photocells have been used in "PulseOx" machines and are commercially available.

In the presently described embodiment, it is important that the sensor provide an accurate reading of pressure during the measurement cycles. Inaccurate readings may be due to a misorientation of the photocell and the LED. In order to minimize any misorientation that would cause an error reading, a circuit board has been chosen that has some longitudinal rigidity. That is, the circuit board, although flexible, resists bending in the flat plane.

As illustrated in FIG. 2, the LED and photocell are disposed on the inside or the finger side 104 of the board. This can create a "tenting" effect because of the variation of pressure around the sensor. That is, there may be a different pressure against the sensor than against other parts of the finger thus providing a false measurement. The tenting issue may be resolved by eliminating non-uniform pressure application about the finger.

In the presently described embodiment, when chamber 78 is pressurized the flexible membrane of finger sleeve 72 transmits the applied pressure directly and uniformly to the finger.

Figure 3C:
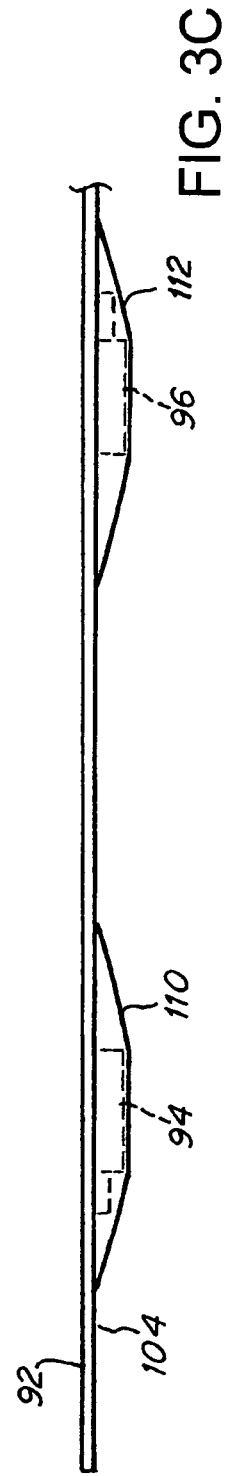
FIGS. 3C and 3D are side views on an enlarged scale of alternative embodiments of the sensor pad disposed in the sensor module.

In one alternate embodiment, illustrated in FIG. 3C, the circuit board 92 is between finger sleeve 72 and the finger, and when chamber 78 is pressurized the force is transmitted through the circuit board and components to the finger. To prevent "tenting", for example, non-uniform force transmission to the finger, the LED 94 and photocell 96 are encased in a conforming material, 110 and 112, respectively. Elements such as the photocell and LED common to the disclosed embodiment are given the same numbers. The conforming material minimizes the non-uniform application of pressure to the finger through the circuit board components when chamber 78 is pressurized. The conforming material may be silicone which is commercially available. One skilled in the art would recognize that there are a variety of conforming materials available that would be suitable. In an embodiment, a medium durometer silicone encapsulates the LED and photocell. The light emitting face of the LED and the light receiving face of the photocell are preferably kept free of the conforming material.

Figure 3D:
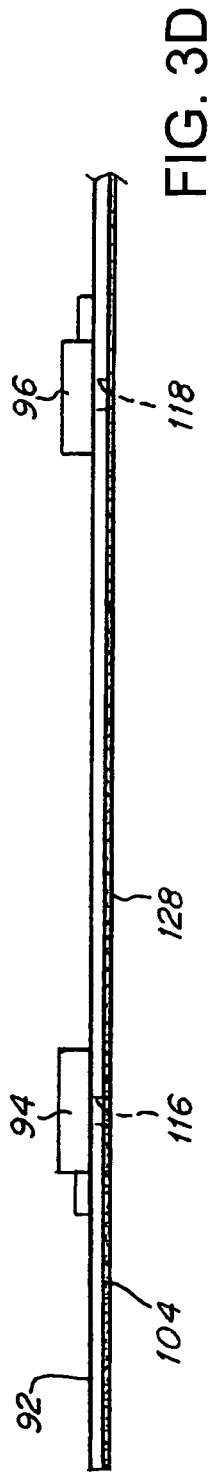

In another alternative embodiment, illustrated in FIG. 3D, the LED 94 and the photocell 96 are disposed on the opposite side of the circuit board. That is, when the flexible circuit board is applied to the finger, the LED and photocell are on the outside of the circuit board such that the circuit board is between the finger and the electronic components. The circuit board includes holes so that light can pass through. Specifically, a hole 116 is disposed below the LED and another hole 118 is disposed below the photocell. This configuration of the LED and photocell further minimizes the possibility of an inaccurate reading due to tenting of the finger sleeve 72, and requires less or no conforming material on the LED and photocell.

The sensor electronics on the board include an amplifier 120 on the circuit board proximate to the photocell. The amplifier enhances the signal received from the photocell. Providing an amplifier proximate to the photocell allows for a better, more robust signal. The signal is less sensitive to noise. The accurate reading of the light signals is important and since the amplifier is placed right at the signal source, the amplified signal closely matches the signal generated from the photocell. This enhances the sensitivity of the sensor. In prior art devices the cables to the electronic signal processors have been shielded to minimized noise and other signal degradation. With the amplifier close to the signal source, the shielding and associated cost, is not necessary.

The sensor 90 is connected to the housing by an electrical lead 124 that connects the housing to the sensor 90. A flat plate electrical connector 126 is attached to the outside of the housing so that the sensor module can become connected to the control module.

The sensor 90 may include a malleable metallic plate 130 disposed along the flexible circuit board so that the sensor may have increased stability. The malleable metal, such as aluminum, also provides a way of positioning the sensor on the finger. In an embodiment, the sensor with aluminum is pressed onto the finger and the aluminum keeps the sensor from moving. An alternative way of ensuring that the sensor 90 does not move is to apply an adhesive material 128 to the inside surface of the sensor so that the sensor sticks to a patient's finger. The sticky surface is represented in FIG. 3D, however, it should be recognized that it could be applied to a variety of sensor structures.

Figure 4:
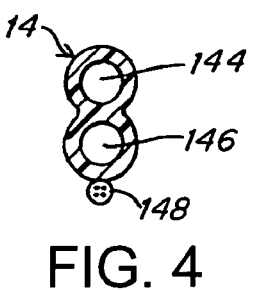
FIG. 4 is a cross-sectional view of the connection between the sensor module and the control module taken along line 4-4 of FIG. 1.

The connection between the sensor module and the control module requires both a fluid (pressure) connection to inflate the proximal and distal air chambers and an electrical connection so that the signals generated by the photocell may be processed. The connector 14, shown in FIG. 1, provides a simple connection. The connector may connect each air chamber port and the sensor individually or, as illustrated, the sensor module may be provided with a short tube 140 which extends from each port in the housing to a connection 142 having at least two lumens, as shown in FIG. 1. This simplifies the connection of the sensor module to the control module by eliminating two thirds of the required connections. FIG. 4 illustrates a cross-sectional view of the connection taken from section lines 4-4 in FIG. 1. As illustrated, the proximal air chamber formed by the finger cuff is supplied with air by passage 144. The distal air chamber formed by the finger sleeve is supplied with air by passage 146. Finally, electrical connection between the sensor module and the control module is provided by wire lead 148.

The control housing 12 contains all the programming and processing code or sequence of executable instructions necessary to use the measurements by the sensor for the determination of the blood pressure of the patient. A screen 180 provides the visual display of the readings for the device. For example, the measured or computed parameters such as pulse pressure and mean blood pressure can be displayed along with trends of diastolic and systolic pressure for a period of time, pulse waveform, and alarm limits. A help screen and information such as a user manual can also be displayed. A variety of display modes are possible. The display may be touch sensitive and the device may operate by the touching the display screen. In an embodiment the user interface may include buttons.

Control panel buttons are provided to the left of the screen and allow the clinician to control the operation of the machine. For example, an "on" button may turn the machine on and off, another button may be included to manually initiate an occlusive pressure reading, as described more fully below.

The control module must have or be in communication with a pump for generating a pressurized gas that can be supplied to the sensor. The pump may be of various kinds known to those skilled in the art and are included in the box.

Additionally, for reasons that are made clear hereinafter, the control module has the capacity to deliver an oscillating pressure signal. There are a variety of mechanisms that can deliver an oscillating pressure signal. The control module may also have a pressure sensor associated with the air supplied to each chamber.

The control module is intended to be a durable component. Thus the housing and its components should be rugged enough to withstand repeated use. The sensor module is intended to be a single patient use item. That is, the sensor module is disposable after a patient has used it. In an alternate embodiment, the sensor module can be sterilized for repetitive use. If a person is monitored for a long period of time, the sensor module is designed to have a limited life such as, for example, a one week life cycle so that after one week, the sensor module should be discarded and a new one used with the patient. The connector cords are intended to be used repeatedly and are designed to be disconnected from both the sensor module and the control module so that they can be replaced more frequently than the control module.

The operation of the sensor with the control module is based on the recognition that when the heart beats, additional blood is forced into the finger. The additional blood obscures more light received by the photocell thus decreasing the signal from the photo-plethysmograph or sensor module. The waveform produced by the pulsation of blood is called the "pulse" signal.

The operation of a blood pressure monitor according to an embodiment of the present invention will now be described. The process of obtaining a continuous blood pressure reading includes at least two modes. A first mode provides an occlusive blood pressure measurement. This is an intermittent procedure that assists in the calibration of the device. The second mode consists of the continuous tracking of the blood pressure using mean blood pressure and pulse pressure. When certain parameters drift outside a predetermined range, an occlusive pressure measurement is triggered to obtain an occlusive reading of blood pressure and then the continuous mode is initiated. The cycle continues to provide blood pressure readings until the device is disconnected from the patient.

Figure 5:
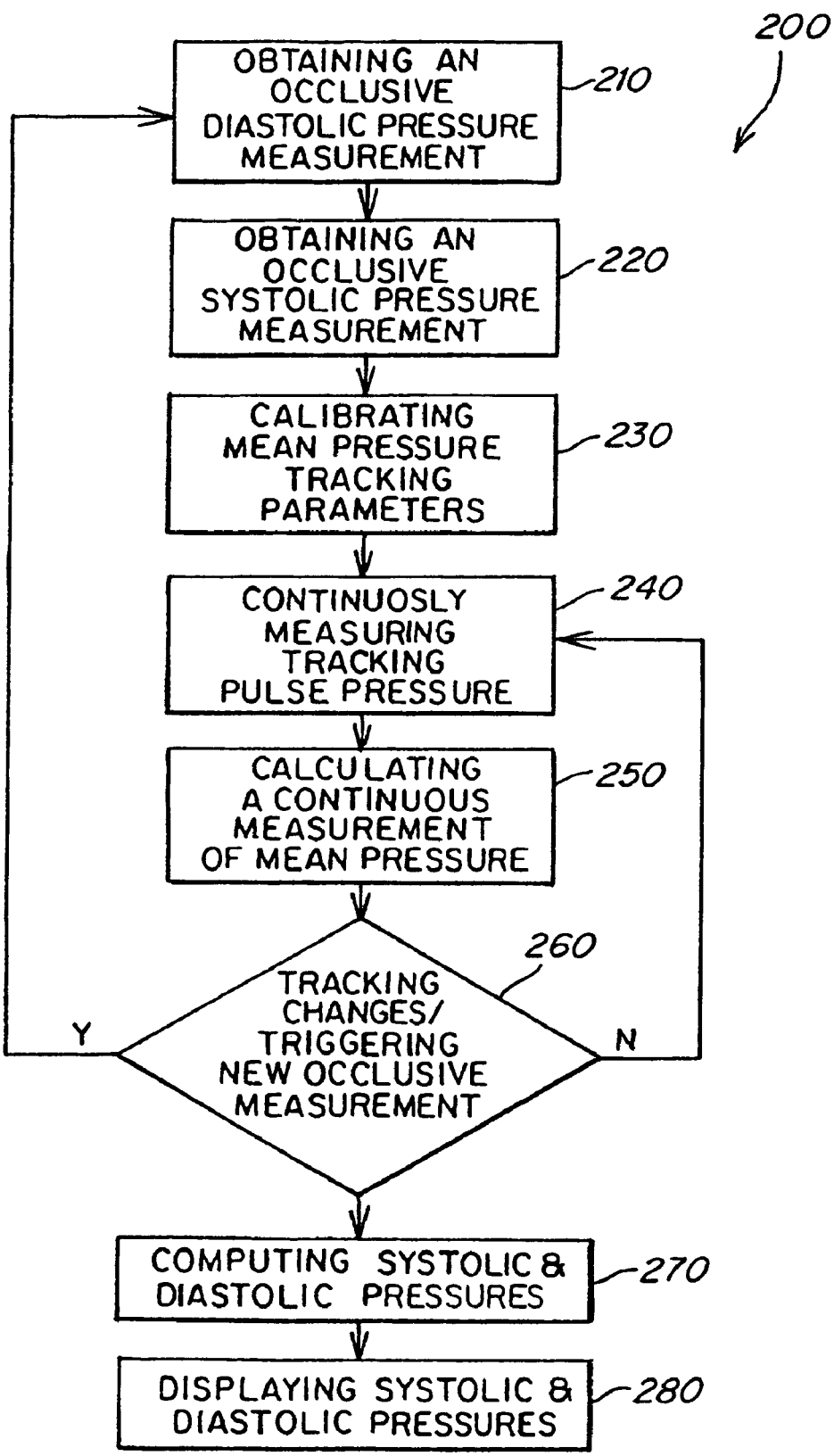
FIG. 5 is a flow chart illustrating a method for measuring blood pressure using a system according to an embodiment of the present invention.

With reference to FIG. 5, the illustrated flow diagram 200 outlines the process of obtaining a continuous blood pressure reading. Each part of the flow chart is described in detail hereinafter. First an occlusive diastolic pressure measurement per step 210 is taken, followed by an occlusive systolic pressure measurement per step 220 being taken. Next the mean pressure tracking parameters per step 230 are calibrated. After the occlusive measurement process, continuous measurement begins. The pulse pressure per step 240 is tracked and blood pressure is continuously calculated per step 250 using a mean pressure calculation. The algorithm tracks changes in pressure per step 260 and when certain conditions are satisfied, a new occlusive measurement is triggered. The systolic and diastolic pressures are then measured and/or computed per step 270. The computed values may be displayed per step 280.

Figure 6:
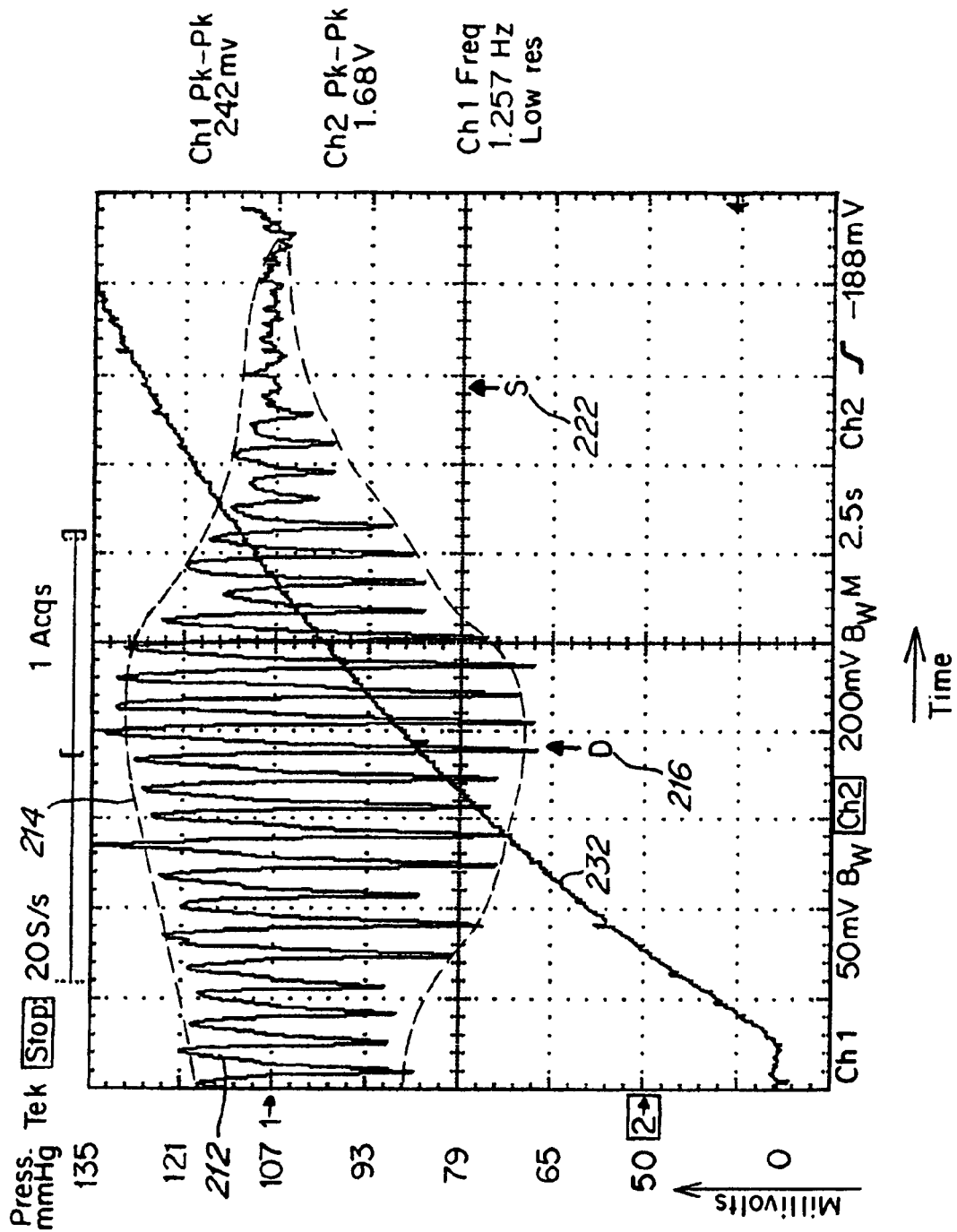
FIG. 6 is a graph that illustrates the pressure reading during an occlusive portion of a pressure measurement according to the present invention.

The occlusive measurement of systolic and diastolic pressure is illustrated by the graph in FIG. 6. The graph illustrates the pressure (mm Hg) versus time (seconds) against the finger inserted in the sensor module while the air is being pumped into the air chambers. Air fills both the proximal and distal chambers. The sensor detects the pulse signal represented by the oscillatory waveform 212 from the plethymograph. As the pressure increases the amplitude of the pulse signal increases until a maximum amplitude. Subsequent increases in pressure causes the amplitude of the waveform 212 to decrease and ultimately the pulse signal disappears. Thus the varying amplitude creates an envelope 214. When the width of the envelope is the greatest (amplitude is the greatest) the diastolic pressure has been reached. Thus, the plot illustrates the diastolic pressure at 216.

The correlation of the amplitude of the pulse signal to the diastolic pressure has been identified only when a finger is fully surrounded by air pressure. As described earlier, the finger sleeve surrounds the finger and when filled with air, pressure is applied to all sides of the finger. The finger cuff extends the pressure further down the finger. If the finger cuff is inflated alone, the same correlation of the amplitude of the pulse signal to the diastolic pressure is not found.

FIG. 6 also illustrates the occlusive measurement of systolic pressure. Once the amplitude of the pulse signal has begun to decrease and diastolic pressure has been measured the finger cuff pressure is increased to occlude the blood. The measurement of the systolic pressure can be performed using only the cuff pressure. As the amplitude of the pulse signal decreases, less blood is pumped through the blood vessel because of the increased pressure. When the pulse signal amplitude decreases to a small fraction of the peak amplitude, the systolic pressure 222 is measured.

Thus, the occlusive systolic and diastolic pressures are measured. It should be noted that there can be variations of the above methods to measure diastolic and systolic pressures which would yield acceptable results. For example, the systolic measurement may be taken by pressurizing the finger cuff alone. After the systolic measurement, the pressure in the finger cuff can be decreased to below the diastolic pressure and the finger sleeve pressure can be increased. Once the two pressures reach an equilibrium (below the diastolic pressure) the pressure can be increased to cause the increase in amplitude of the pulse signal. Once the maximum amplitude is identified, the diastolic pressure has been achieved.

Using diastolic and systolic pressure measurements the mean blood pressure can be calculated. An accepted equation for calculating the mean blood pressure (BP) is:

$$\text{mean BP} = \tfrac{1}{3}\, \text{Systolic} + \tfrac{2}{3}\, \text{Diastolic} \qquad \text{Equation 1}$$

In an embodiment, having calculated the mean blood pressure and measured values of the systolic and diastolic pressure, the next calculation is the first gain factor. The first gain factor is the rate of change of photocell voltage divided by the rate of change of mean blood pressure. It is calculated by determining (tracking) the change of photocell voltage and pulse signal amplitude for a change in pressure, chosen to be between 30 mm Hg and 50 mm Hg. The line 232 in FIG. 6 represents the increase in pressure over time that determines the diastolic and systolic pressure.

Figure 7:
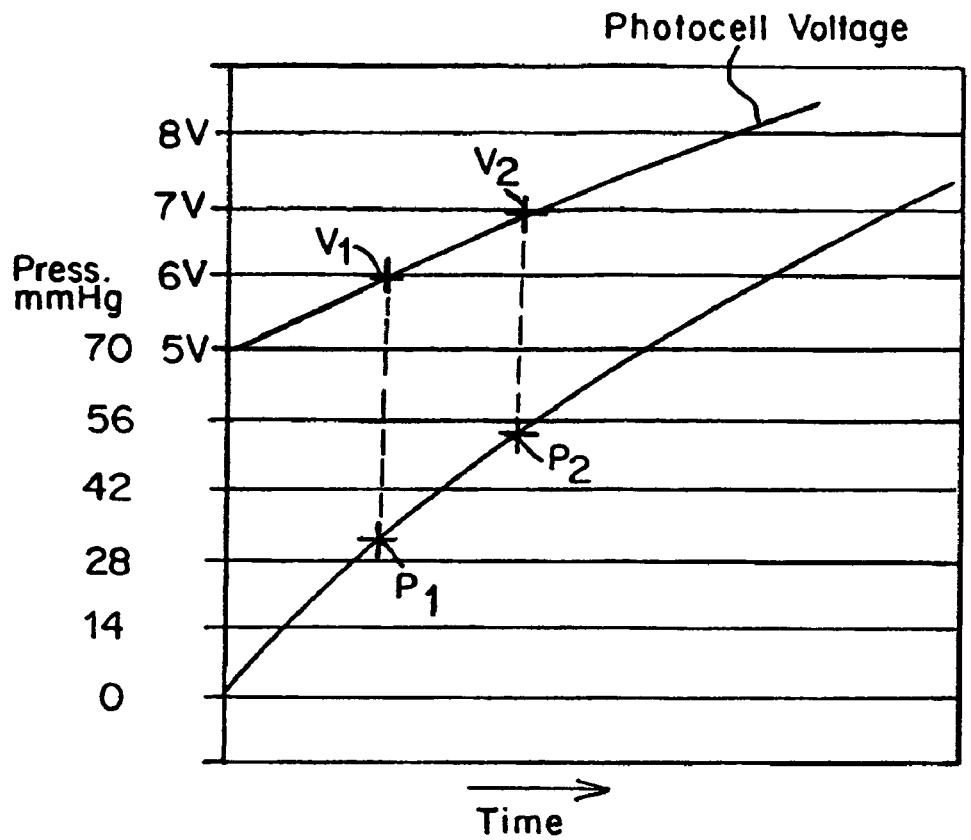
FIG. 7 is a graph illustrating the change in photocell voltage and pressure vs. time that details a portion of FIG. 6 and illustrates the information used to determine the "gain factor" of an embodiment of the system.

FIG. 7 is an expanded view of the pressure change for a given change in photocell voltage. As illustrated, the gain is determined by calculating the change in voltage for a given change in pressure. P1 represents 30 mm Hg and P2 represents 50 mm Hg. The calculated voltage change V1-V2 is (6 volts-7 volts) and the gain is 1 volt per 20 mm Hg. This first gain factor is used in the continuous determination of blood pressure described hereinafter. A new first gain factor is determined each time an occlusive blood pressure measurement is taken.

Figure 9:
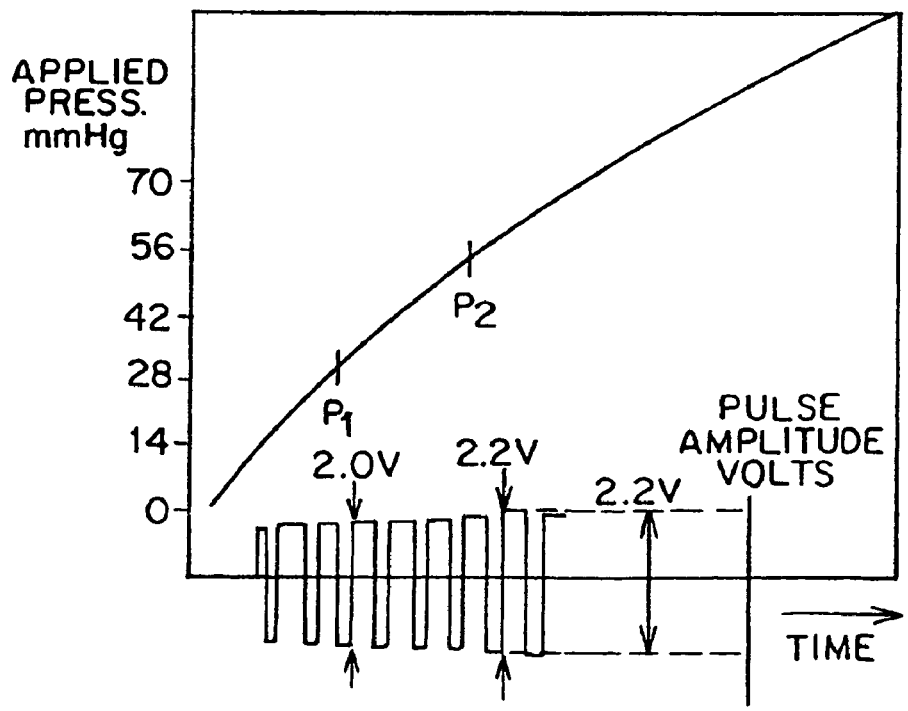
FIG. 9 is a graph indicating the applied pressure versus time.

A second gain factor is computed as the rate of change of pulse amplitude divided by the rate of change of mean blood pressure. The second gain factor is computed at the same time by calculating the change in pulse amplitude for a given change in pressure as illustrated in FIG. 9. The pulse amplitude increases from 2 volts to 2.2 volts as the applied pressure is increased from 30 mmHg to 50 mmHg, and thus the second gain factor is 0.2 volts per 20 mmHg.

The blood pressure monitor then transfers into the second mode of continuous blood pressure monitoring. The two parameters that are measured and calculated to determine the continuous blood pressure in accordance with an embodiment are mean blood pressure, as defined in Equation 1 above, and the pulse pressure. Pulse pressure is the difference between the systolic pressure and the diastolic pressure. If one were to have a blood pressure 120 over 80, the pulse pressure would be 40 mm Hg. The pulse pressure is determined first.

The calculation of the pulse pressure relies on the principle that an artery responds to pressure as a gauge pressure. That is, the artery will respond the same way to an applied pressure whether from inside the artery or outside the artery, just with an opposite sign. Accordingly, if one applies a known pressure on the outside of the artery, the pressure inside the artery will respond in a known manner. The described embodiment of the invention uses this principle to determine the pulse pressure by inducing a known pressure signal (sinusoidal) of known amplitude and frequency. The monitoring system applies an AC external pressure to the finger to induce a pulse signal into the arteries and thus into the plethysmograph. The combined heart pulse and induced pulse signal is amplified, and analog filters separate the combined signal into the separate heart pulse signal and the induced pulse signal respectively. The frequency of the induced pressure signal should be either above or below the normal pulse frequency so that the signals can be properly differentiated.

Figure 8:
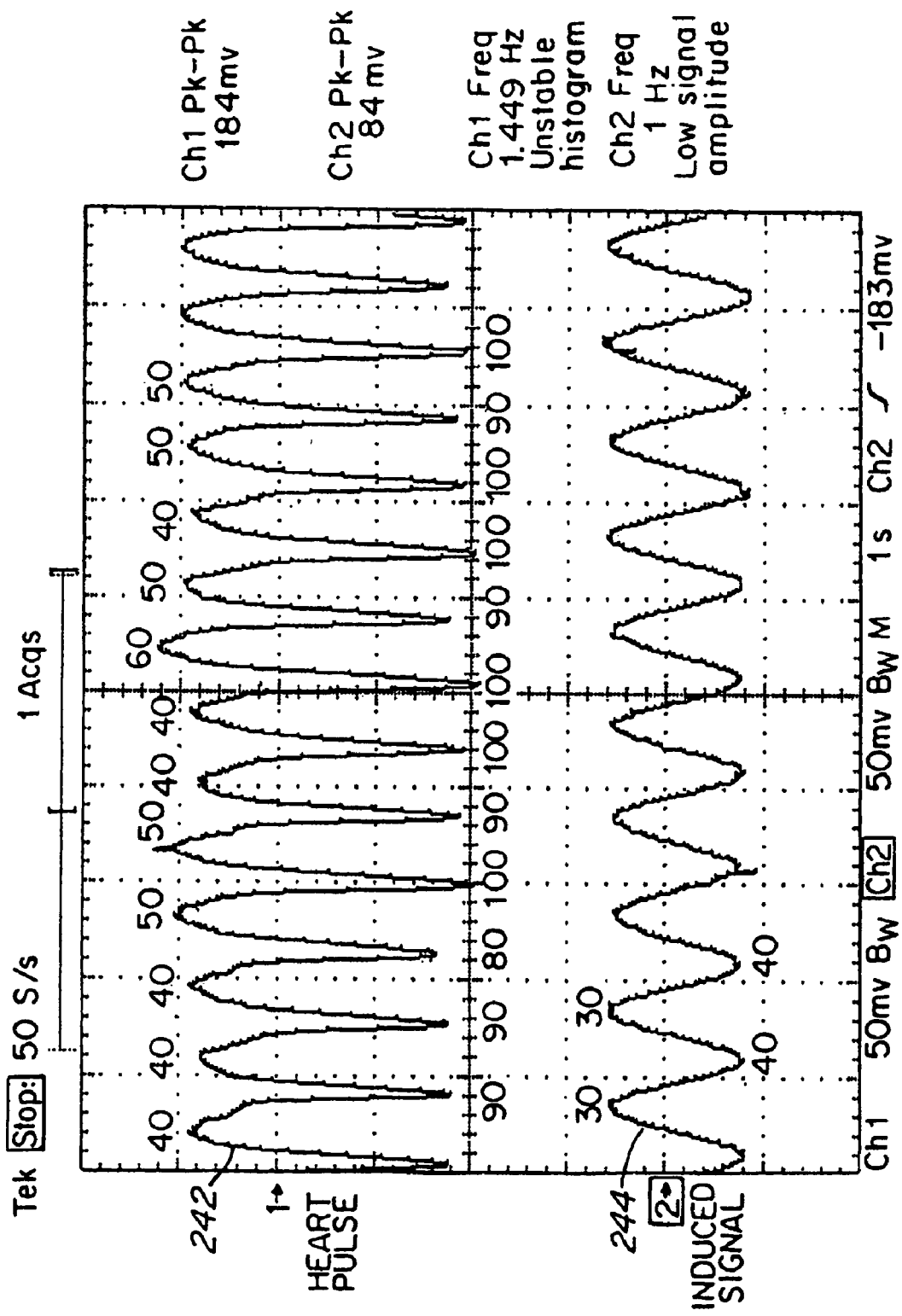
FIG. 8 is a graph of the induced signal and heart pulse signal which are measured by the sensor module.

As described herein before, the sensor reads the combined heart pulse and the induced signal which is then separated to determine the pulse pressure. FIG. 8 illustrates the waveforms of the separated induced and heart pulse signals. The X axis of the chart represents time in seconds, the y axis represents signal amplitude. The top waveform 242 represents the heart pulse. The bottom waveform 244 is the induced pulse signal. The pulse pressure is calculated from the relative amplitude of the two signals. The following equation is used to calculate pulse pressure:

pulse pressure=(pulse amplitude/induced signal amplitude)*induced pressure   Equation 2

For example, if an induced pressure such as an AC external pressure is applied to the finger of 20 mm Hg and the heart pulse signal (amplitude) is twice as large as the induced signal (amplitude) then the pulse pressure is 40 mm Hg.

The finger contains venous blood as well as arterial blood. The blood in the veins of the finger also responds to an induced pressure signal. The contribution of the venous response to the induced pressure constitutes an error which should be minimized or preferably eliminated. To that end, a constant pressure (DC pressure) is applied to the finger by the finger cuff and finger sleeve during the measurements. This applied pressure forces much of the blood out of the veins. This static pressure is chosen to be sufficient to minimize the amount of blood in the veins while not becoming uncomfortably tight for the patient. For example, 40 mm Hg is thought considered sufficient to push virtually all the blood out of the veins while not being uncomfortable.

The proper selection of the frequency of the induced pressure signal can also assist in the reduction of any error caused by venous blood. For example, a relatively high frequency induced pressure signal is selected because the venous blood responds less to the high frequency induced pressure than the arterial blood. Because the pulse pressure is determined during each occlusive measurement (systolic BP-diastolic BP), a correction factor can be determined for the pulse pressure by an induced pressure measurement method and then applying the correction factor to subsequent measurements.

Mean blood pressure is determined next. It should be noted that arteries are composed of a lining of elastin (elastic tissue) within a layer of fibrin (relatively inelastic tissue). Consequently, arteries have a non-linear stress/strain relationship. In particular, they become much less elastic or compliant as mean arterial pressure increases. Because the induced pressure applied to the finger is constant, the induced signal amplitude is a direct function of arterial compliance. In particular, as mean blood pressure increases, the arterial compliance decreases and the induced signal amplitude decreases. During continuous tracking of blood pressure, the applied pressure to the proximal and distal finger cuffs has a mean pressure of approximately 40 mmHg. The value of the photocell voltage is continuously monitored, and any change in the photocell voltage is converted into a change in mean blood pressure by dividing the change in photocell voltage by the first gain factor. That change is added to the value of mean blood pressure obtained in the last occlusive BP measurement for the first mean blood pressure value. Similarly the amplitude of the induced pulse signal is continuously monitored, and any change in the pulse amplitude is converted into a change in mean blood pressure by dividing the change in pulse amplitude by the second gain factor. That change is added to the value of mean blood pressure obtained in the last occlusive BP measurement for the second mean blood pressure value. The geometric mean of these two values is then computed to obtain the subject's mean blood pressure:

mean blood pressure=√(first mean blood pressure*second mean blood pressure)   Equation 3

An alternate method for tracking mean blood pressure is also used by the system of the present invention. After calibration by the occlusive measurements the finger cuffs are inflated to a nominal static pressure such as 40 mm Hg. The values of induced pulse amplitude and dc photocell voltage are measured and their product, mean blood pressure signal (meanbpsig), is saved. During the continuous blood pressure monitoring mode the static cuff pressure is then continually adjusted to maintain the value of meanbpsig equal to the initial value measured at calibration. In particular, if meanbpsig decreases, as happens if the mean blood pressure rises, the static cuff pressure is increased until meanbpsig is equal to its initial value. Because the mean blood pressure seen by the monitored digit equals the arterial mean blood pressure minus the static cuff pressure, increasing the cuff pressure reduces the effective mean pressure to the digit. The effective digit mean pressure is continually maintained at the value measured during calibration. The arterial mean pressure is then the mean pressure measured at calibration plus (or minus) the change in static cuff pressure post calibration. This method has the advantage that the gain factors of induced pulse amplitude versus mean blood pressure and dc photocell voltage versus mean blood pressure do not need to be measured since they are not directly used in the measurement of mean blood pressure changes.

The methods of computing mean blood pressure from two parameters, for example, photocell voltage change and induced pulse amplitude change, are independent of changes in arterial compliance from vasoactive drugs, for example, that could cause either one or the other parameter, by itself, to give an incorrect value for mean blood pressure.

Once the mean blood pressure and the pulse pressure are determined, Equation 1, above, is modified to determine the diastolic and systolic pressures as provided below:

Systolic BP=mean blood pressure+⅔ pulse pressure      Equation 4

Diastolic BP=mean blood pressure−⅓ pulse pressure      Equation 5

Because the same equation is used to calculate mean blood pressure from the measured values of systolic and diastolic pressure and to calculate the systolic and diastolic from measured values of pulse pressure and mean pressure the inaccuracy of the split between systolic and diastolic pressure (⅓ and ⅔) is factored out.

The measurement of blood pressure continues until a hemodynamic parameter changes sufficiently to cause the control module to begin another occlusive pressure measurement. Some of the parameters that would cause an occlusive measurement to occur are: pulse pressure; mean pressure; and pulse rate. If any of these parameters change more than, for example, 10% in a predetermined time cycle, the control module begins a new occlusive measurement. A new occlusive measurement is also started after a predetermined amount of time. For example, occlusive measurements may be performed every 5-10 minutes as a check on the system. The predetermined period may increase or decrease depending on specific factors. Also, there will be a manual start for an occlusive measurement so that a clinician can begin an occlusive measurement for whatever reason.

Figure 10A:
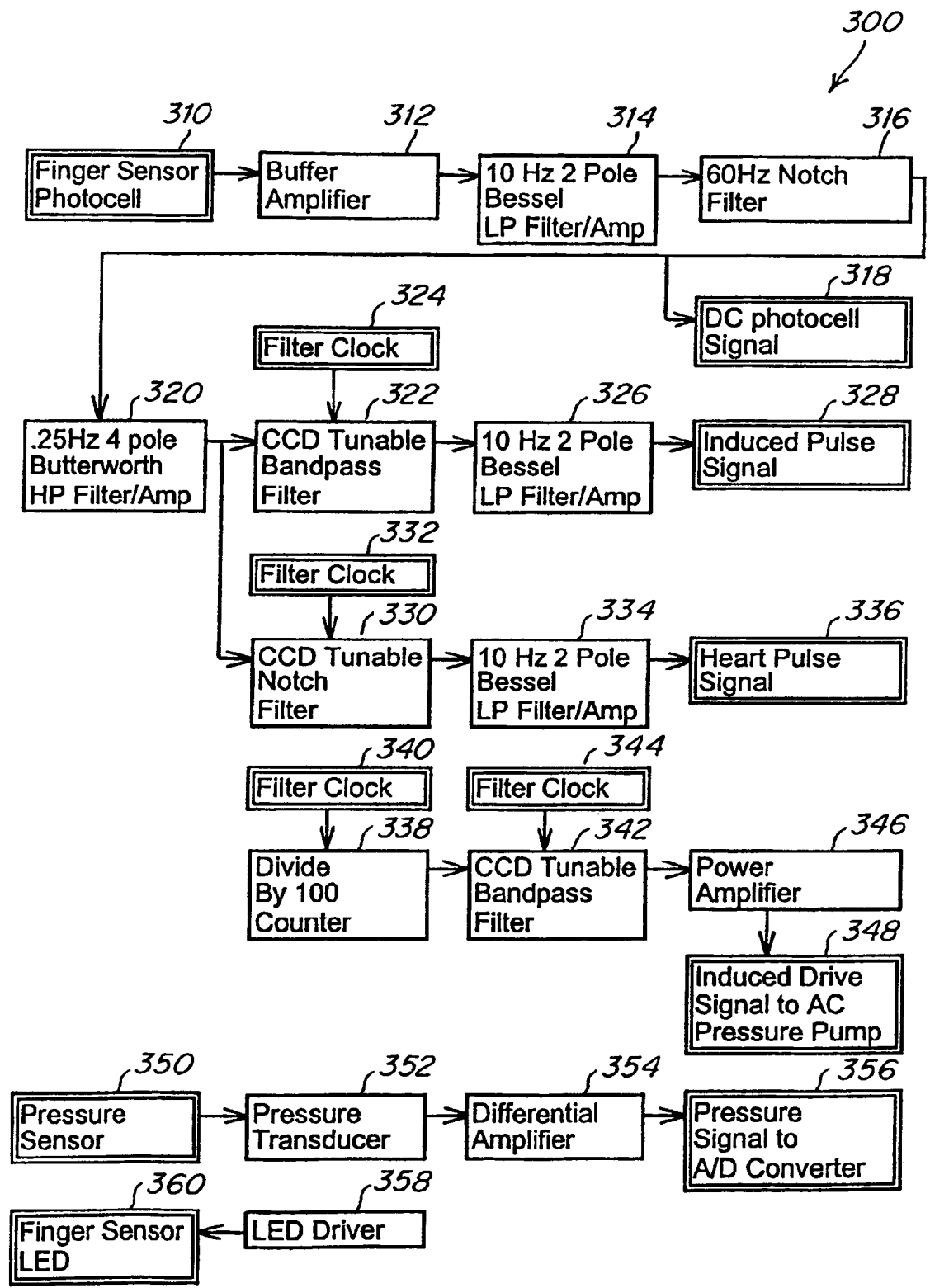
FIG. 10A is a block diagram illustrating the analog signal processing circuitry in accordance with an embodiment of the blood-pressure monitoring device.

FIG. 10A is a block diagram illustrating the analog signal processing circuitry 300 in accordance with an embodiment of the blood pressure monitoring device. A signal obtained from the photocell sensor 310 placed proximate to the finger is amplified by a buffer amplifier 312. This signal is indicative of the arterial pressure.

The signal is then processed using two sets of filters including a two-stage low pass filter and a two-stage high pass filter. In particular, the amplified signal is first filtered using a 10 Hz, two-pole Bessel low pass filter 314 to remove any high frequency noise. The signal is then filtered using a 60 Hz notch filter 316 to remove any noise driven by 60 Hz sources. A DC level of the photocell signal 318 can be obtained from the output of the low pass filter 314 and notch filer 316. The signal is then processed through a 0.25 Hz, four-pole Butterworth high pass filter 320 to remove low frequency noise in the physiological signals.

The signal is then processed using switched capacitor filters to separate the induced pulse signal 328 from the heart pulse signal 336. A switched capacitor tunable band pass filter 322 centered at the frequency of the induced pulse signal along with the four-pole Butterworth high pass filter 320 and a 10 Hz, two-pole Bessel low pass filter 326 are used to separate the induced pulse signal 328. These three stages 320, 322, 326 are adjusted to obtain a moderate response. The heart pulse signal 336 is obtained using a switched capacitor tunable notch filter 330 centered at the frequency of the induced signal frequency. This filter 330 minimizes any distortion of the heart pulse signal but rejects the induced pulse signal. A 10 Hz, two pole Bessel low pass filter 334 is used in combination with the notch filter to obtain the heart pulse signal. The Bessel filters 314, 326, 334 provide a constant time delay as they do not introduce any phase shift distortion. The Bessel filters 326, 334 are placed after the switched capacitor filters to remove high frequency switching noise introduced by these filters. The induced pulse signal 328 can be characterized as having a frequency of 1.5 times the heart pulse signal 336.

The analog processing circuitry 300 also provides the induced drive signal to an AC pressure pump 348. A switched capacitor tunable band pass filter 342 coupled to a power amplifier 346 are used in this portion of the circuitry. A pressure signal is provided to the A/D converter using a signal measured by a pressure sensor 350 and processed by a differential amplifier 354. Further a LED driver 358 provides a signal to the finger sensor LED 360.

FIGS. 10B1 through 10B4 illustrate an exemplary circuit diagram of an analog processor showing the circuit components discussed with respect to FIG. 10A. The flow diagram discussed with respect to FIG. 10A can be implemented using different values of circuit components and even different components.

Figure 11:
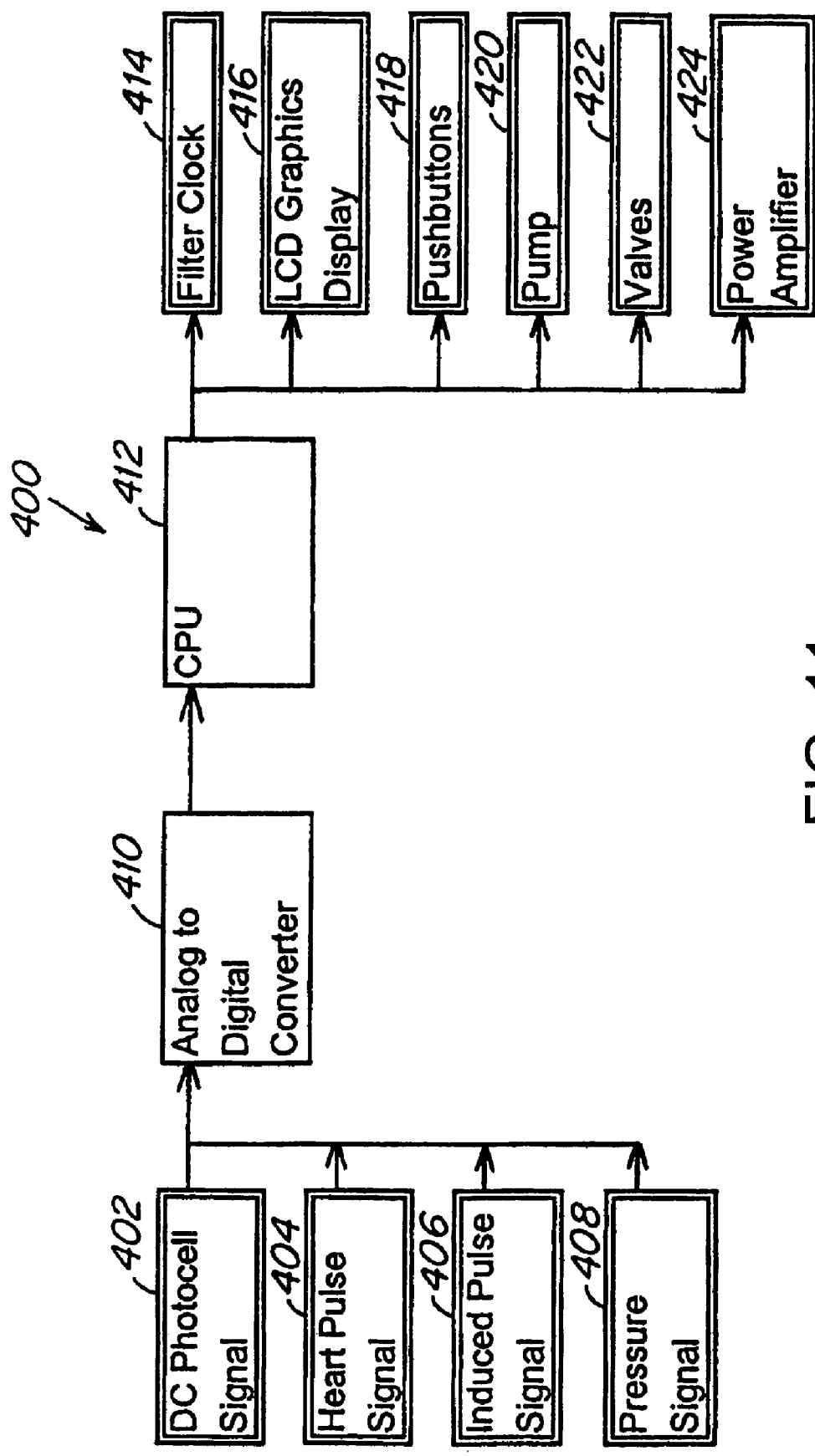
FIG. 11 is a block diagram illustrating the digital signal processing circuitry in accordance with an embodiment of the blood pressure monitoring device.

FIG. 11 is a block diagram illustrating the digital signal processing circuitry of the blood pressure monitoring device. The signal 402 obtained by the DC photocell, the signal 404 indicative of the heart pulse, the signal 406 indicative of the induced pulse and pressure signal 408 from the inputs to the A/D converter 410. The output of the A/D converter forms an input to the processing unit (CPU) 412 which provides an input to a plurality of functions such as a filter clock 414, LCD graphics display 416, user interface buttons 418, a pump 420, valves 422 and a power amplifier 424.

Figure 12:
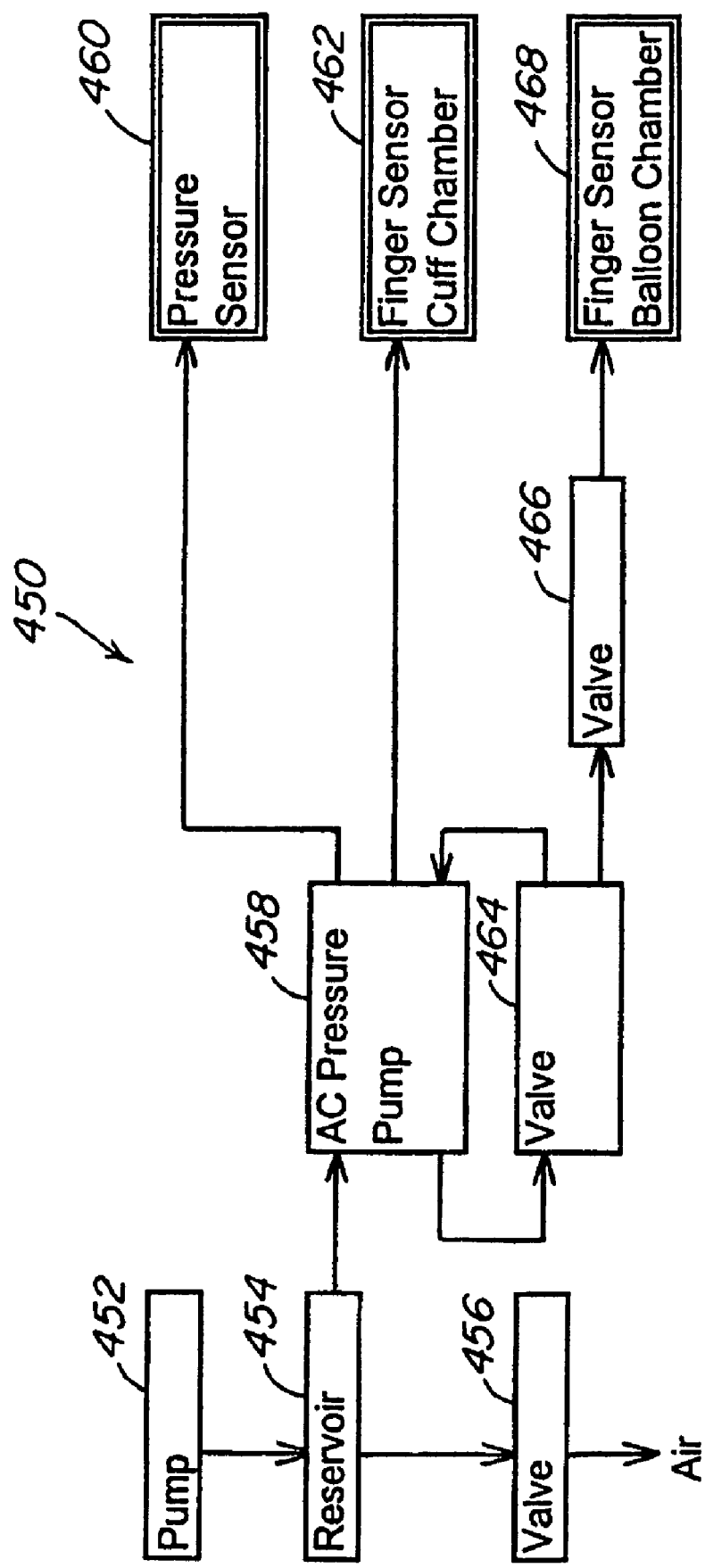
FIG. 12 is a block diagram illustrating the pneumatics of an embodiment of a blood-pressure monitoring device.

FIG. 12 is a block diagram illustrating the pneumatics of the blood pressure monitoring device. A pump 452 is in fluid communication with a reservoir 454. At least one valve 456 is coupled to the reservoir 454. The pressure sensor 460 and finger sensor cuff chamber 462 are coupled to an AC pressure pump. A finger sensor balloon chamber 468 is in communication with a valve 466 which in turn is in communication with the AC pressure pump.

Figure 13A:
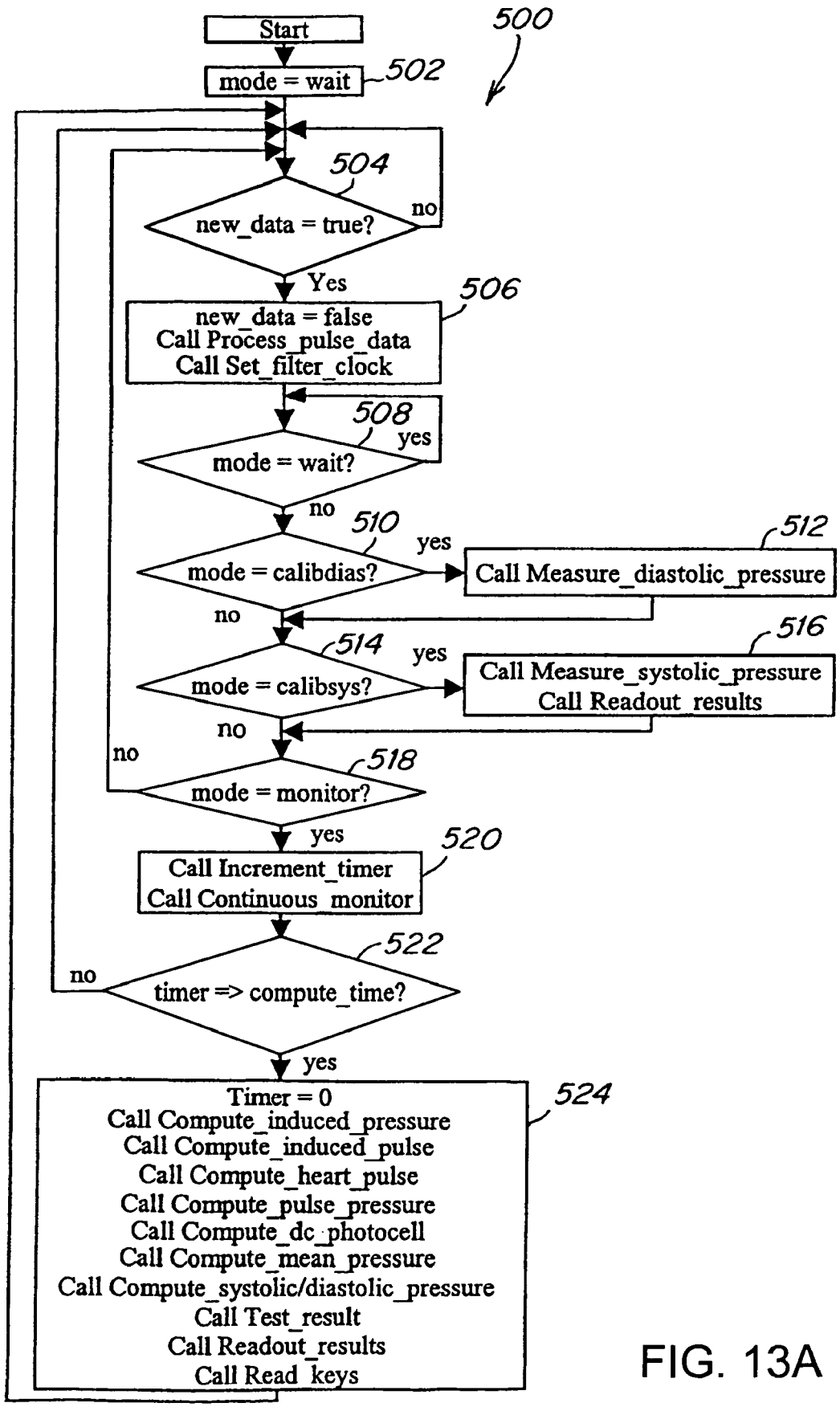
FIGS. 13A and 13B are a flow diagrams of a method to non-invasively provide a continuous measurement of blood pressure in accordance with an embodiment of the blood-pressure monitoring device.
Figure 13B:
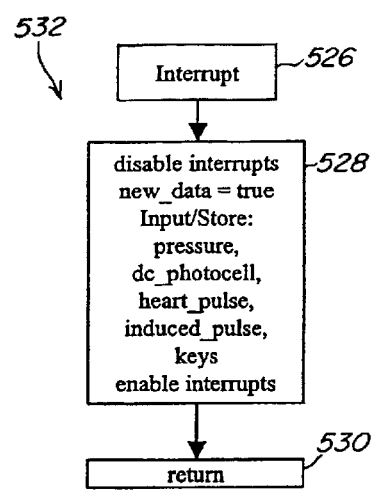

FIGS. 13A and 13B are flow diagrams of a method to non-invasively provide a continuous measurement of blood pressure. As described hereinbefore, the photo-plethysmograph (sensor) induces a reference signal. The measured signal obtained by the photocell is a composite signal of the induced reference pulse signal and the heart pulse signal. There are at least three measurement modalities in the system to measure blood pressure continuously: a calibration mode, a tracking mode wherein pulse pressure is tracked; and a continuous mode that includes continuously measuring mean blood pressure. The software or executable instructions in the processor first ascertains if new data has been received such as the photocell data, heart pulse data, and induced pulse data, per step 504. If new data has been received, the processing includes the execution of the instructions associated with processing pulse data and setting of the filter clocks per step 506.

The process flow continues to then calibrate the diastolic pressure measurement using a peak in a pulse plethysmograph reading which is an occlusive measurement of blood pressure of almost the entire finger (at least from the second joint to the distal finger tip).

The tracking of the pulse pressure signal uses an external variable pressure to calibrate on a continuous basis the response of the pulse plethysmograph to vascular pressure. The amplitude of the heart pulse signal and induced pulse signal are tracked, and ratiometric methods are used to get pulse pressure using the pulse signal and DC level signal from the photocell. Calibration of the blood pressure monitor occurs continuously to account for the compliance of the vasculature by applying the external variable pressure.

The continuous mode includes processing the mean blood pressure measurement continuously per steps 520 and 524. Two signals are used to account for the changes in vascular compliance and track mean blood pressure signals. For example, the amplitude of the induced pulse signal and photocell voltage are used to calibrate changes in mean blood pressure. Alternate ways to track changes in mean blood pressure include using the DC voltage of the photocell and the induced pulse signal, or a closed loop feedback process requiring no calibration, such as counteracting changes to the mean blood pressure by changing cuff static pressure.

As described with respect to FIGS. 13A and 13B, the top level process determines the monitoring mode [wait, calibrate diastolic (calibdias), calibrate systolic (calibsys), or continuous BP monitoring (monitor)] to schedule the appropriate subroutines or executable instructions to process patient data, compute derived parameters, and output to the display the measured physiological parameters and waveforms. The top level process runs continuously in a loop once invoked, and waits for new data to be available from the interrupt handler (new_data=true) for processing.

The interrupt handler sequence of instructions as described in FIG. 13B is invoked by a hardware timer nominally every 16.7 ms. It causes the analog-to-digital converter to sample the input signals, for example, but not limited to pressure transducer signal, dc photocell voltage, heart pulse signal, and induced pulse signal, convert the signals to digital format, and transfer the data to the processor. Digital input signals from the front panel pushbutton keys are also sampled and transferred to the processor. The interrupt handler sets a flag (new_data=true) informing the top level process that new data is ready for processing.

Figures 1, 14A:
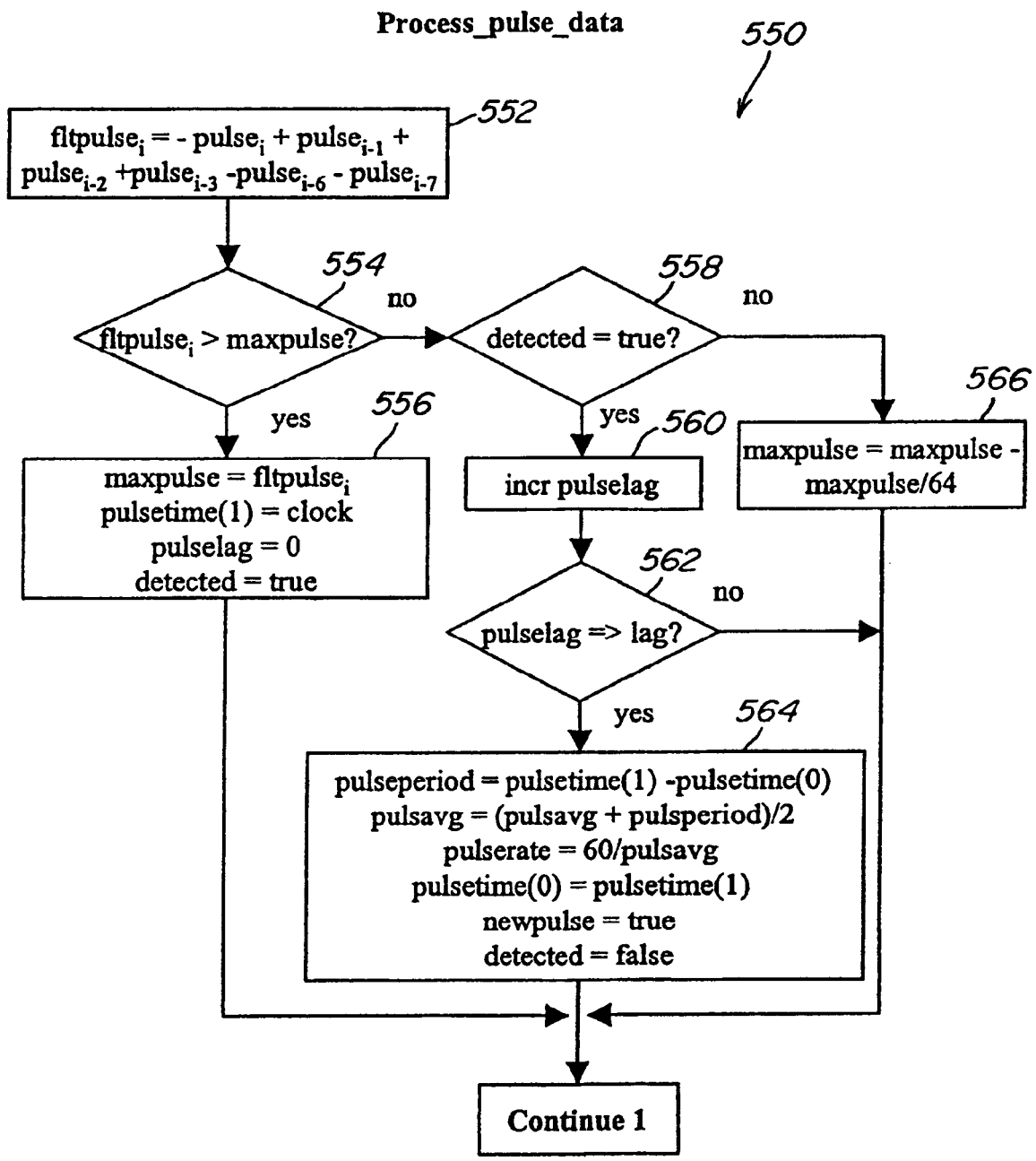
FIGS. 14A-14P are detailed flow diagrams of the software processing modules identified in the process flow diagram of FIGS. 13A-13B.
Figures 2, 14A:
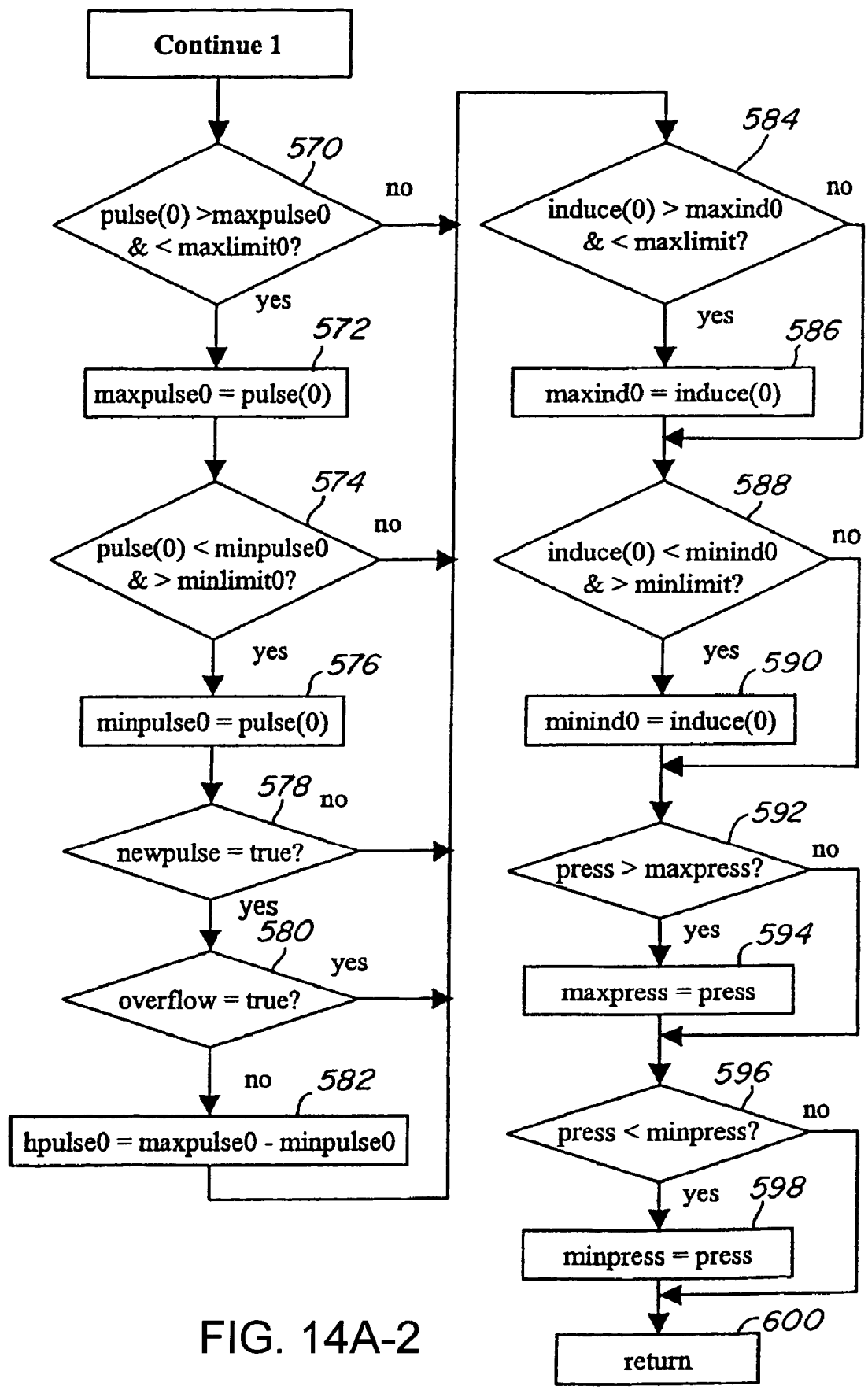

The process_pulse_data subroutine as described in FIGS. 14A1 and 14A2 digitally filters the input heart pulse signal to enhance the pulse signal (fltpulse). It looks for a peak in the pulse signal (maxpulse), and waits for a time (lag) to ensure that a bigger peak is not found. It computes the pulse period to the last pulse (pulseperiod), and computes an average pulse period (pulsavg). It computes pulse rate in beats-per-minute (60/pulsavg), and sets flags (newpulse, detected). It also measures the peak-to-peak amplitude of the heart pulse (hpulse0), induced pulse (ipulse0) and induced pressure (ipress0).

Figure 14B:
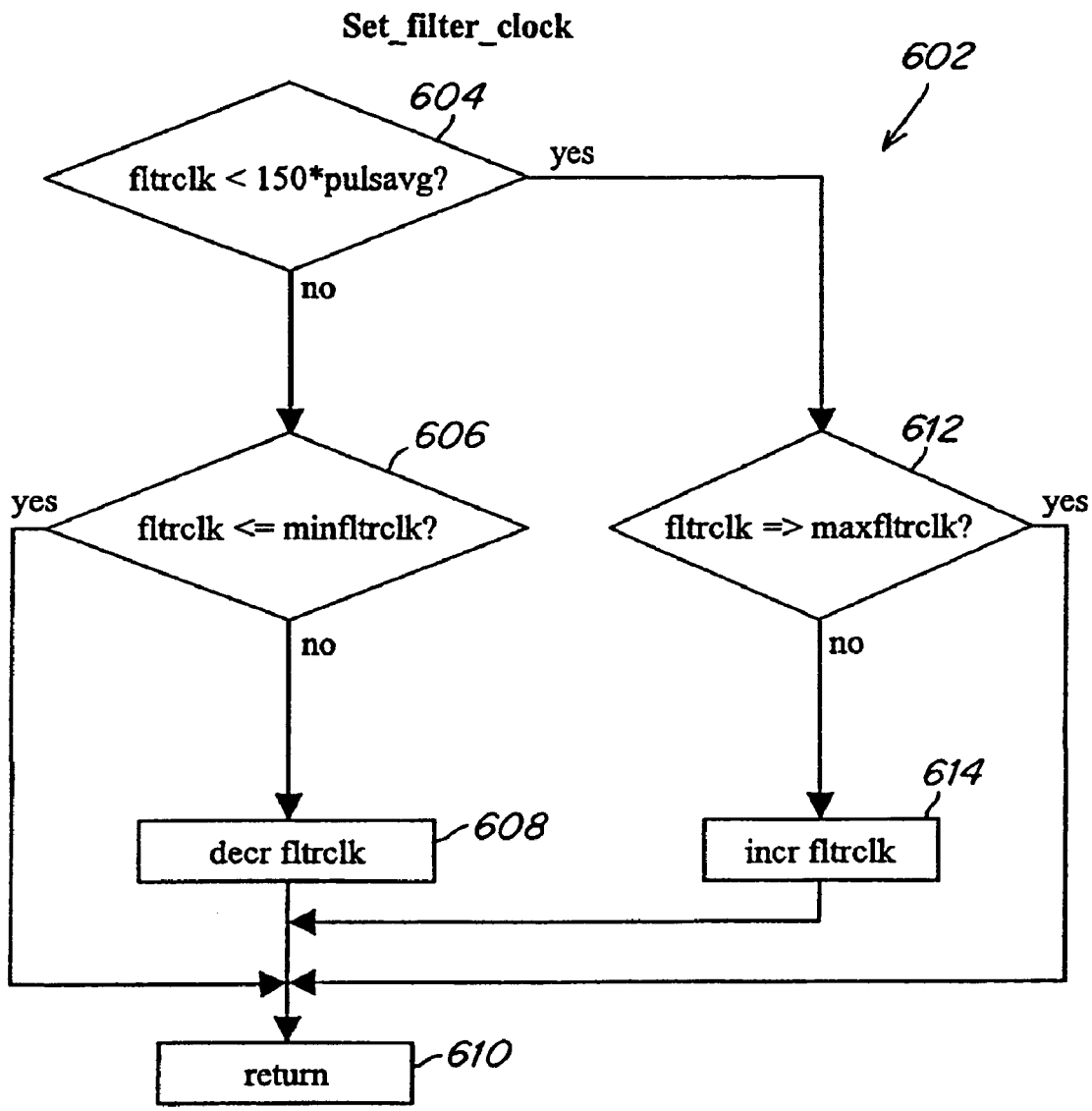

The set_filter_clock subroutine as described in FIG. 14B sets and controls the induced signal frequency to nominally 1.5 times the pulse rate. The switched capacitor filters require a clock at 100 times their center frequency, and the subroutine controls the hardware to output a clock at 150 times the pulse rate. If the clock is too fast, it decrements the clock rate. Similarly if the clock is too slow, it increments the clock rate.

Figure 14C:
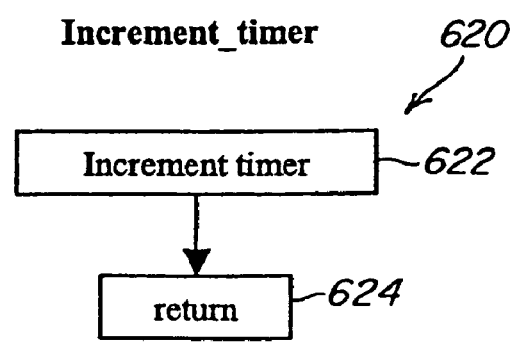
Figure 14D:
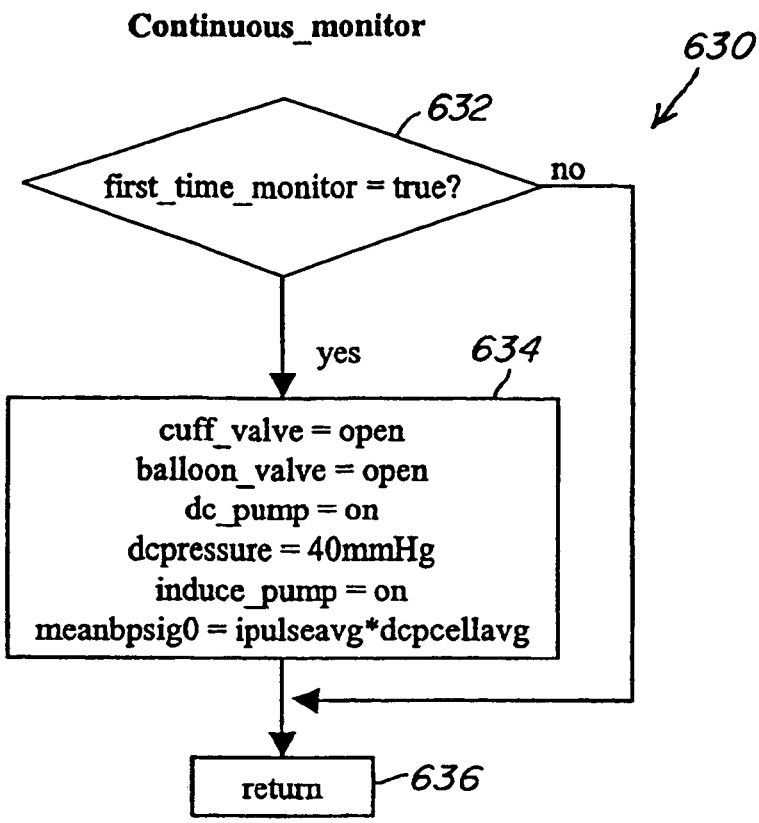
Figure 14E:
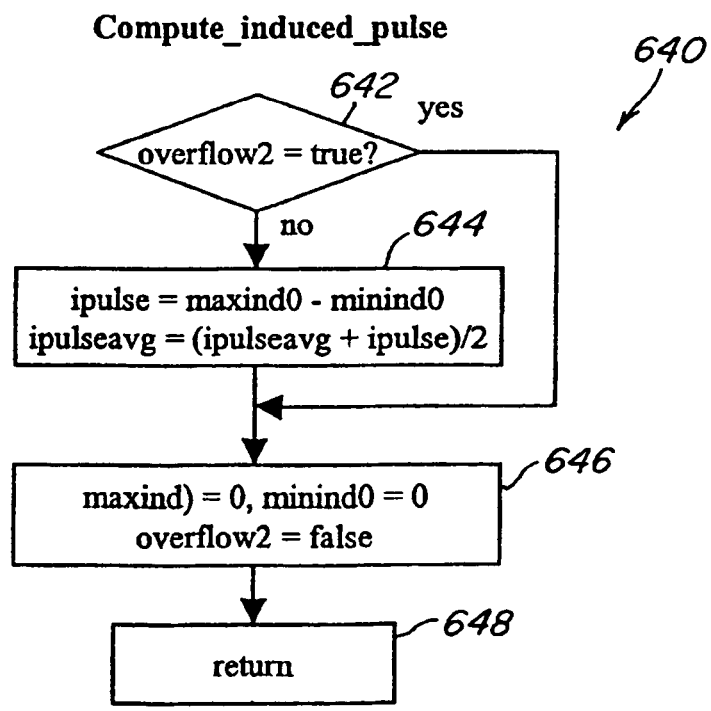
Figure 14F:
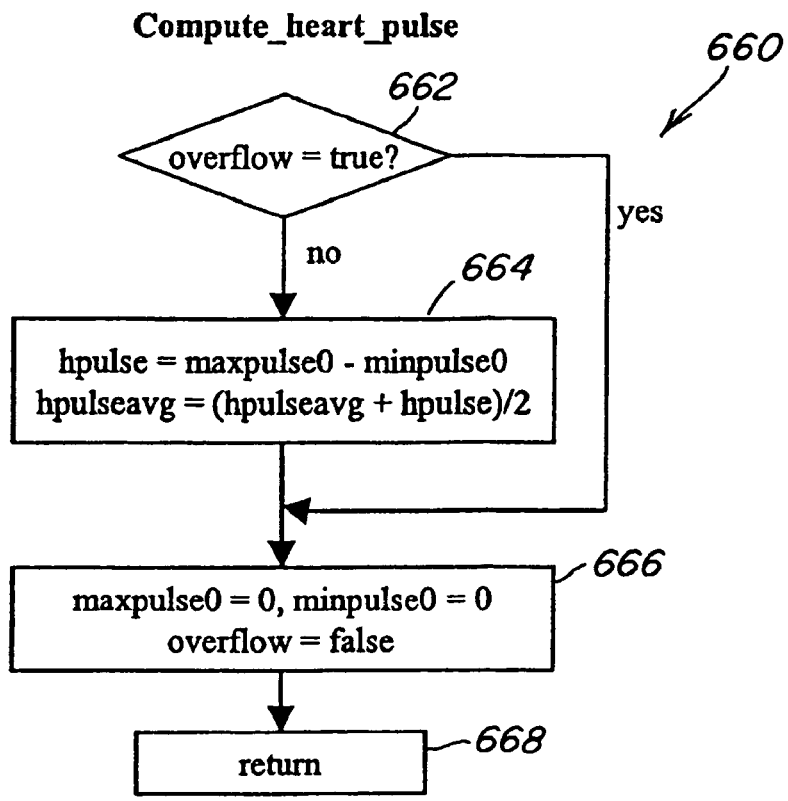
Figure 14G:
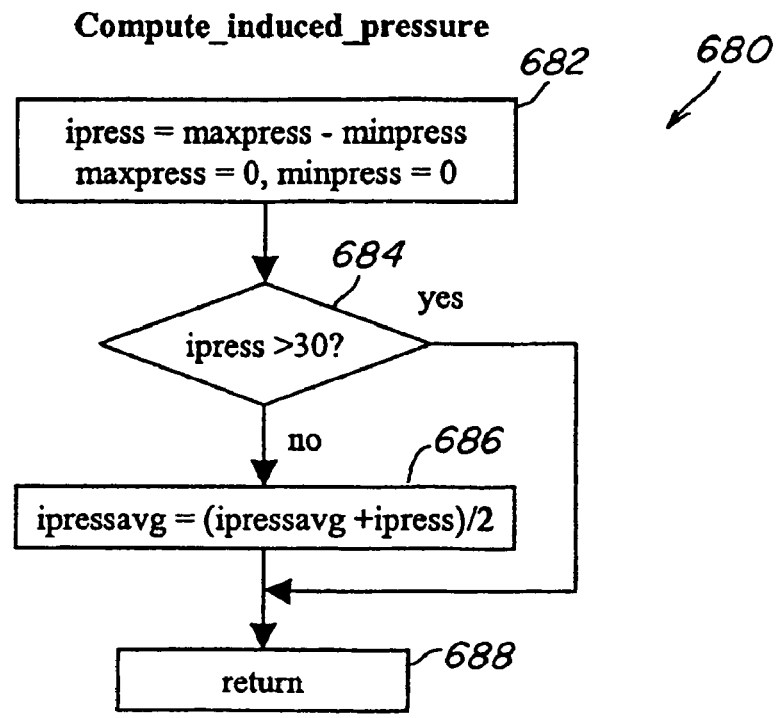
Figure 14H:
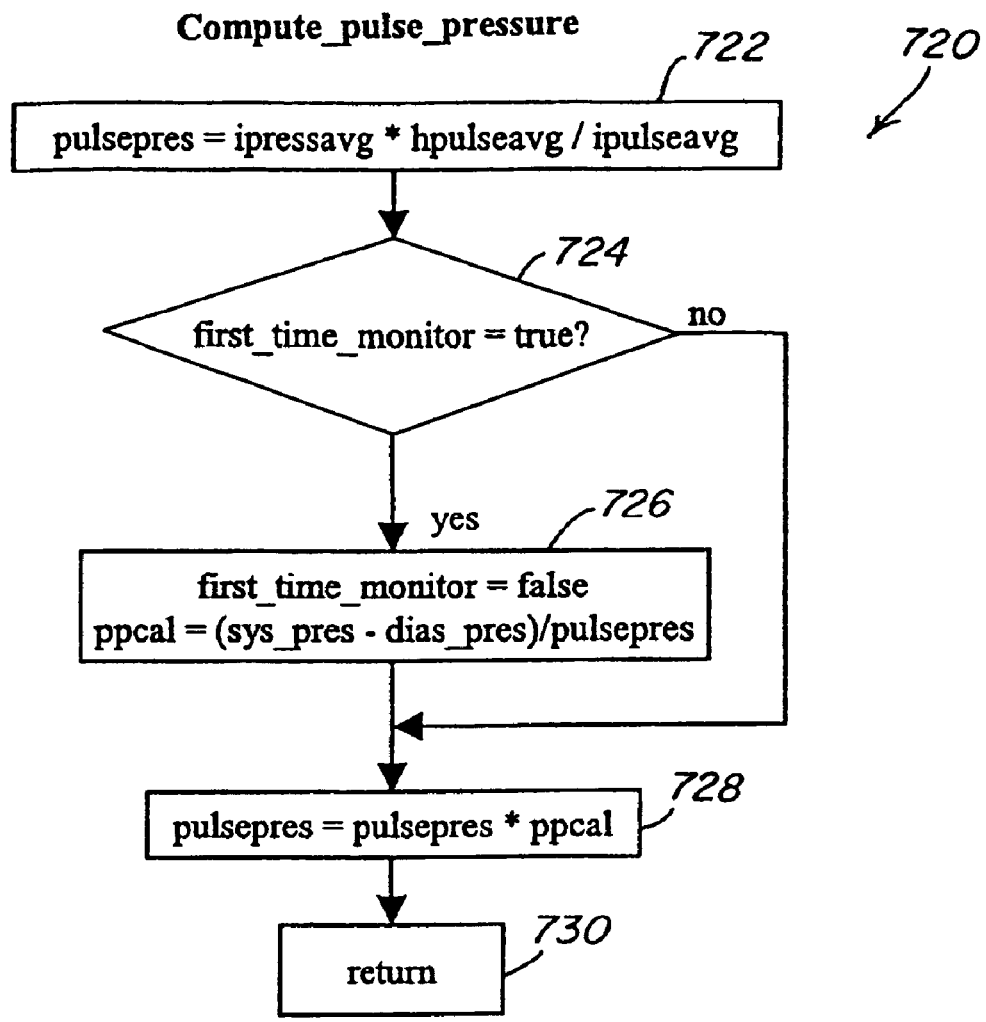
Figure 14I:
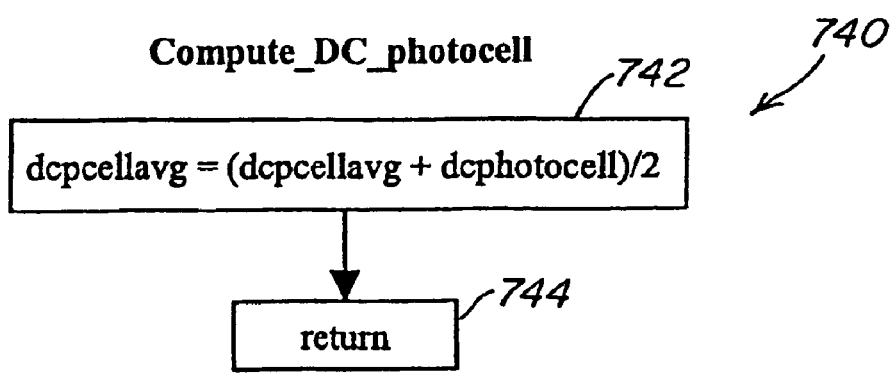
Figure 14J:
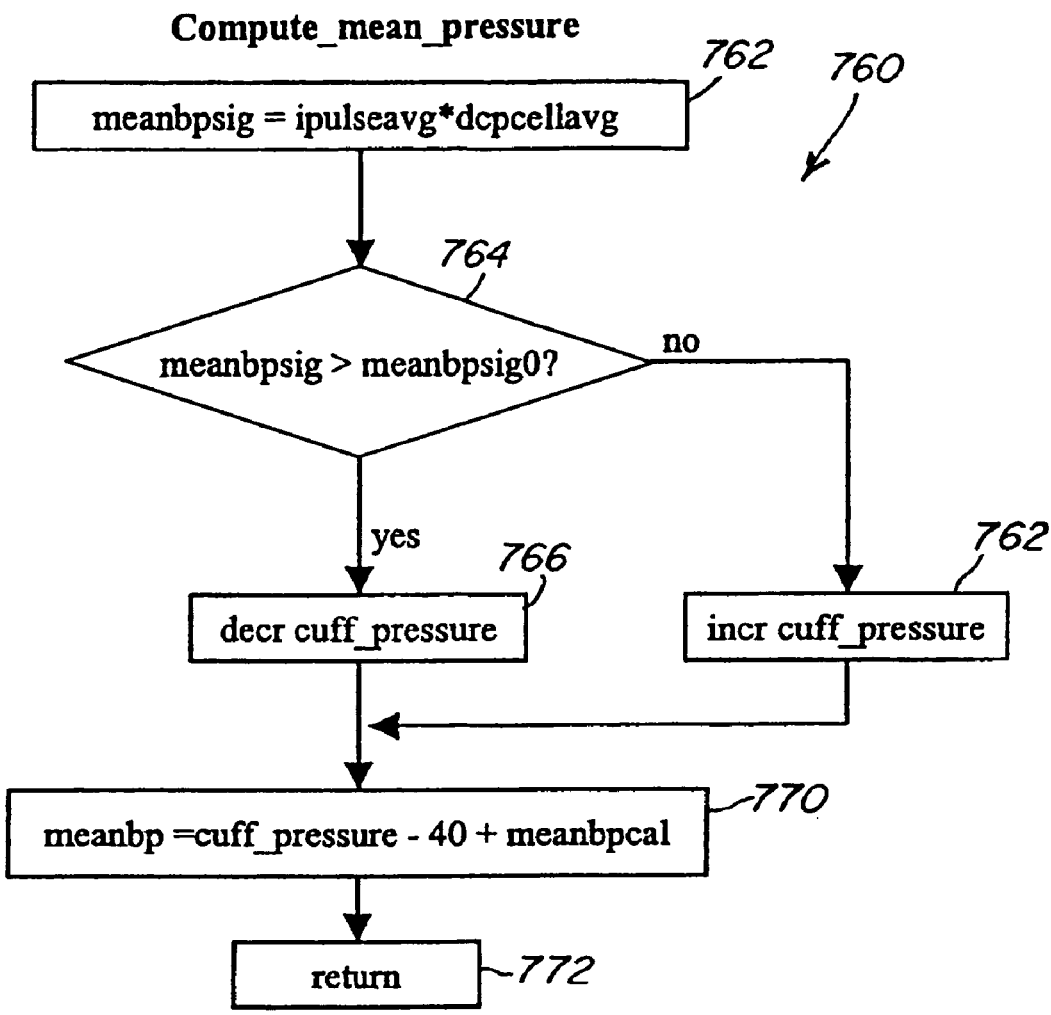
Figure 14K:
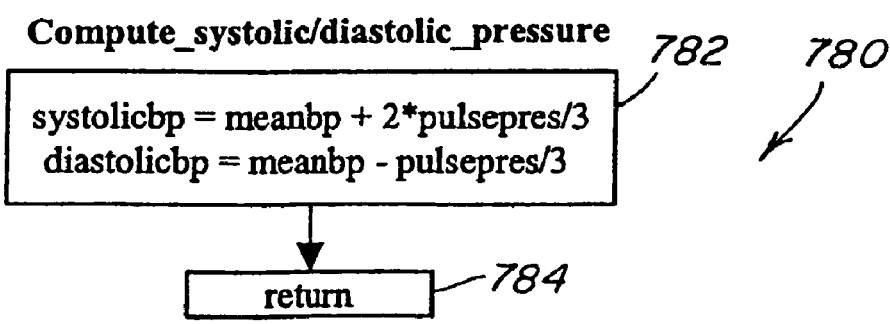
Figure 14L:
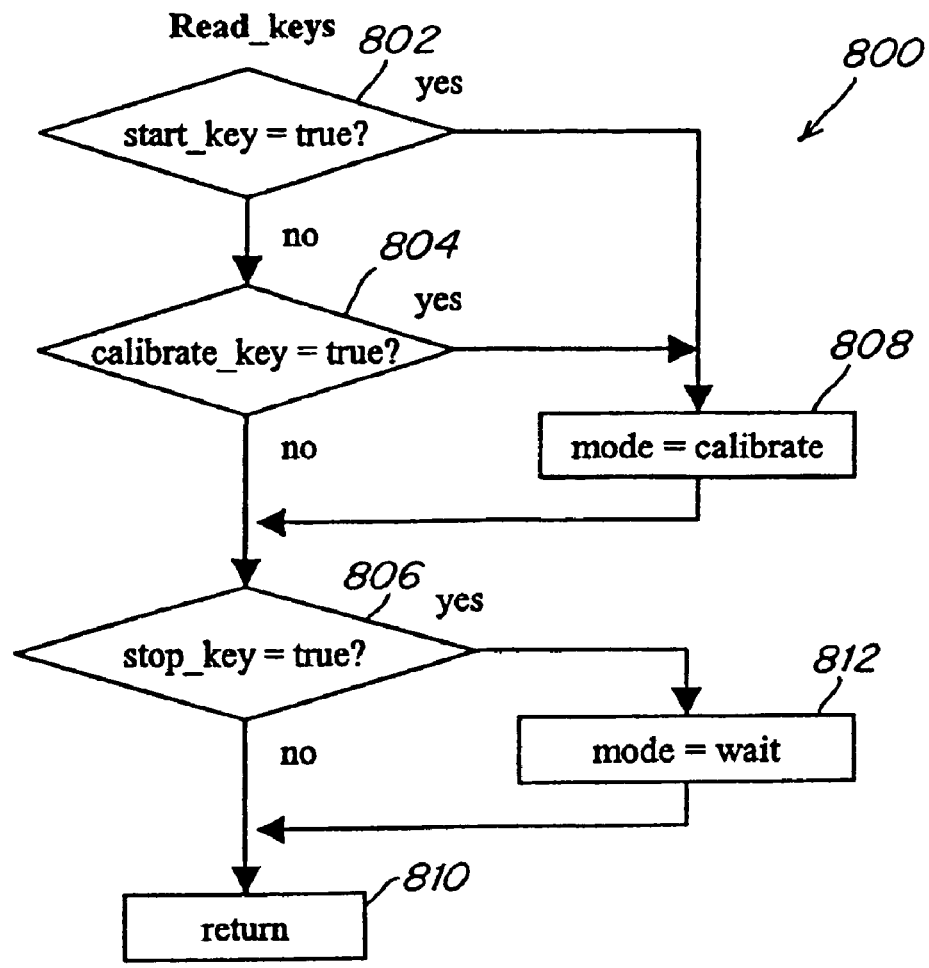
Figure 14N:
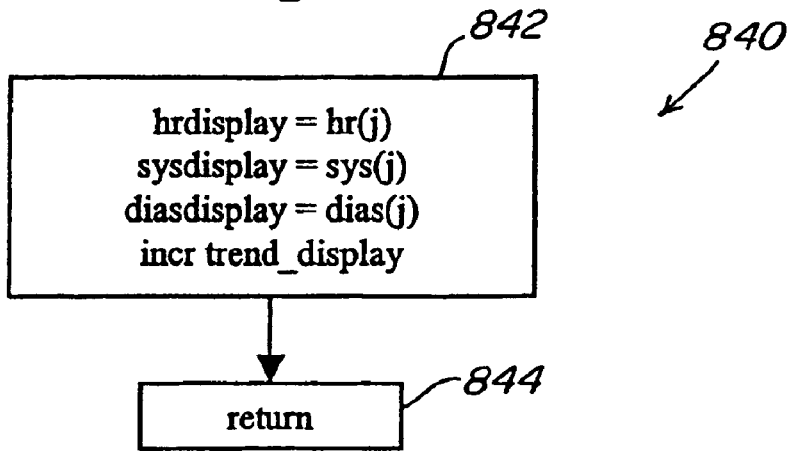
Figure 14M:
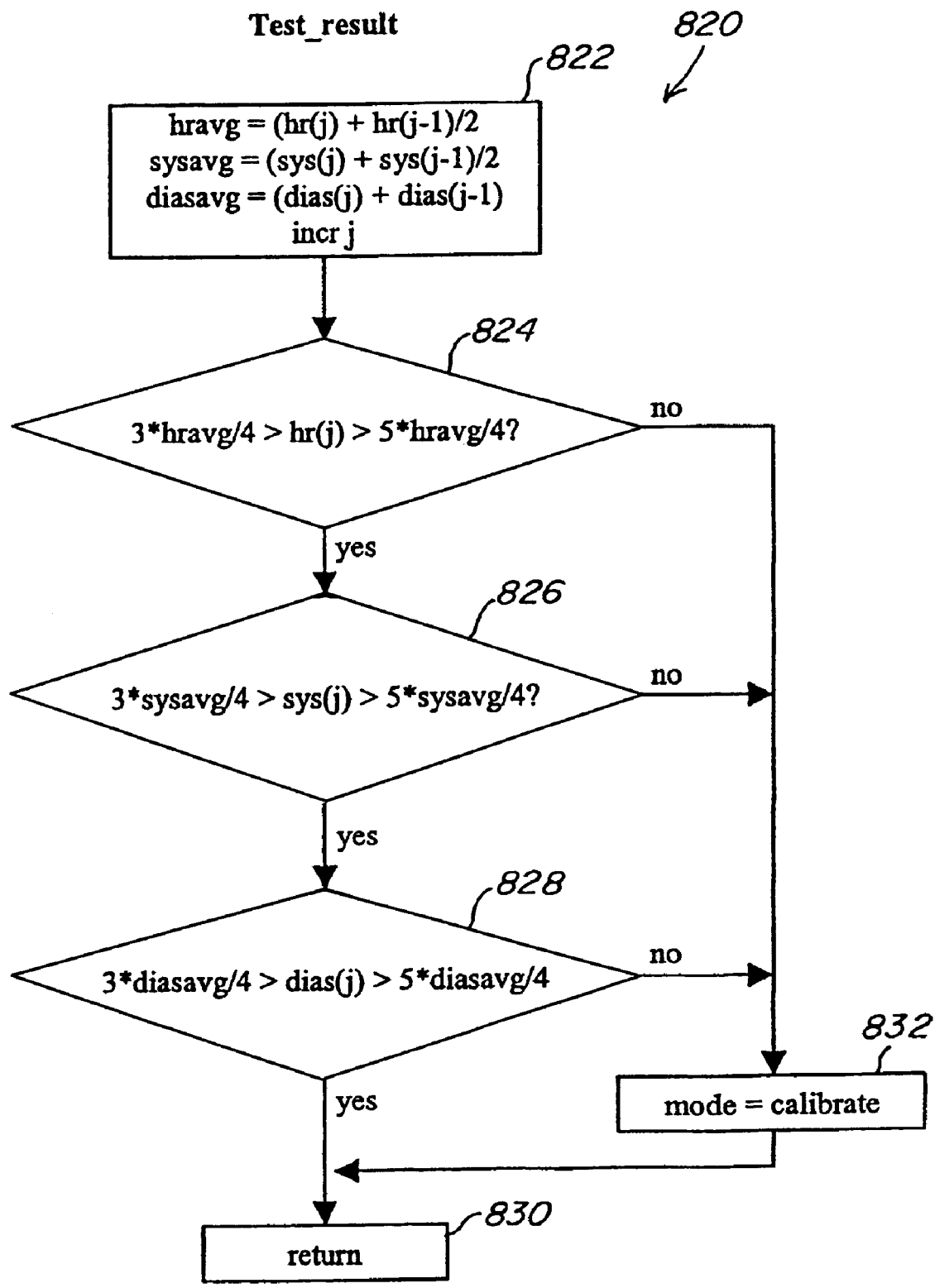
Figure 14O:
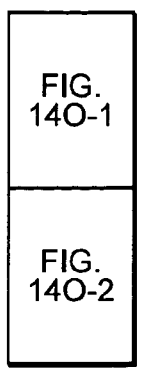
Figures 1, 14O:
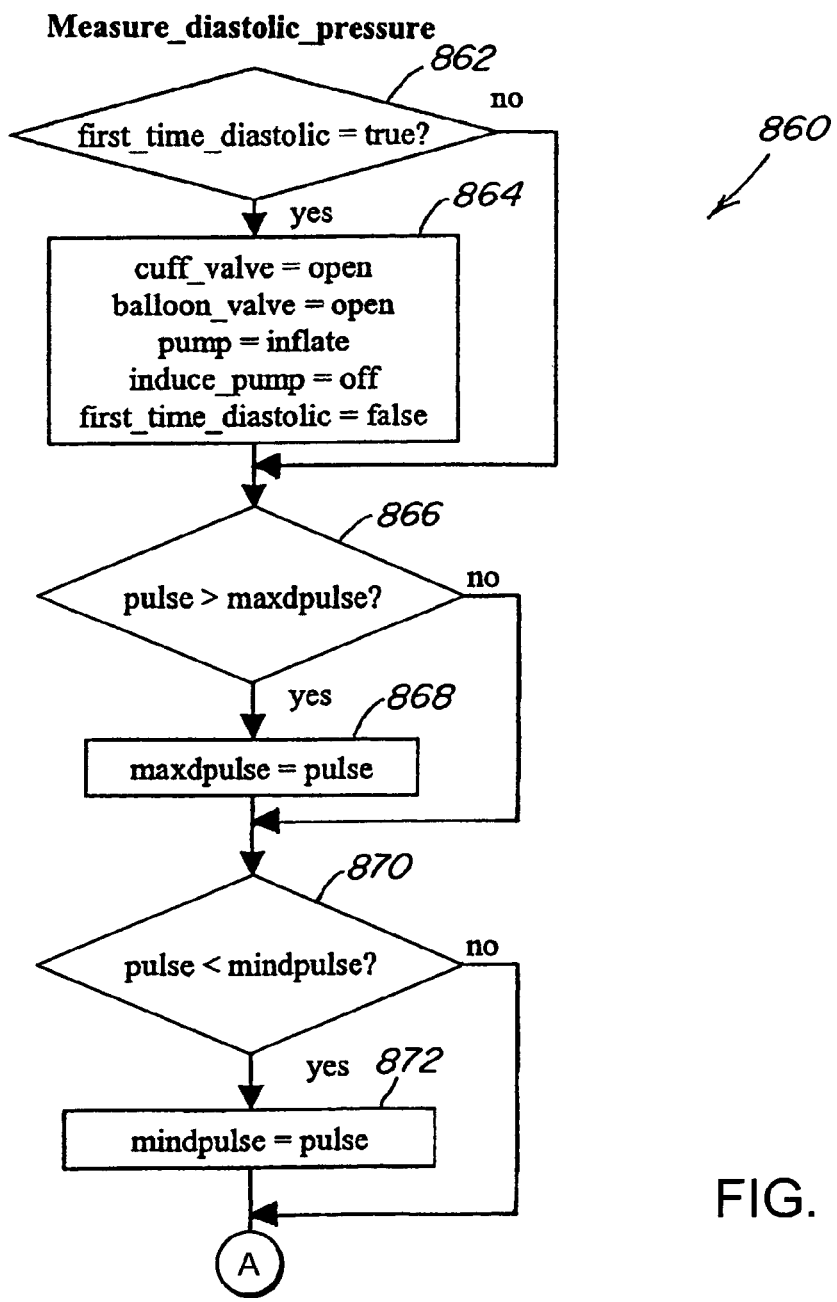
Figures 2, 140:
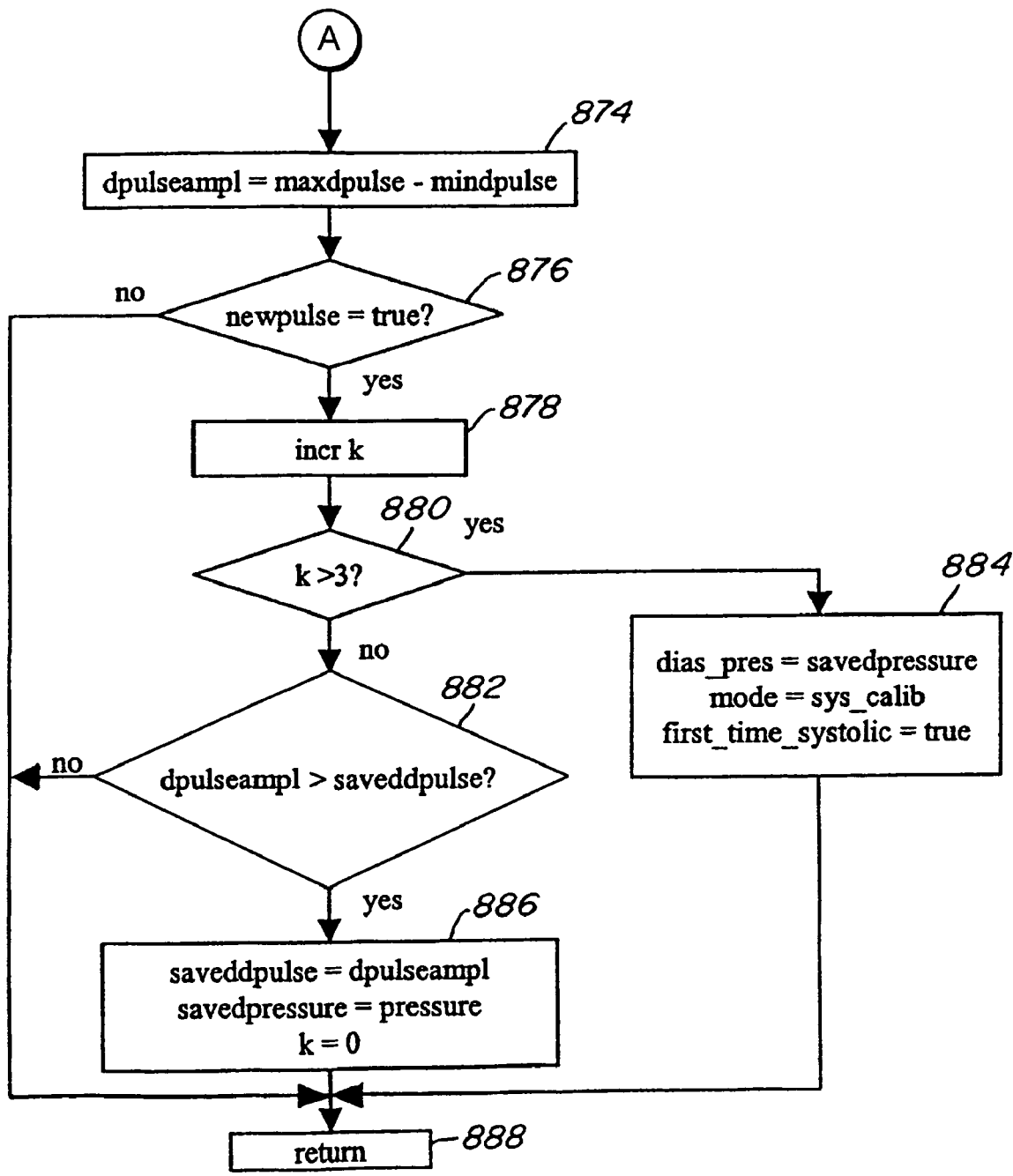

The measure_diastolic_pressure subroutine as described in FIG. 14O sets and controls the pneumatics to measure diastolic blood pressure by occlusion (cuff valve open, balloon valve open, induced pressure pump off, pump inflating cuff). It looks for the peak in the heart pulse signal, saves the pressure at the peak, and outputs that pressure as diastolic blood pressure.

Figure 14P:
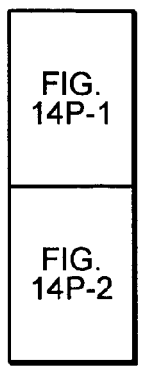
Figures 1, 14P:
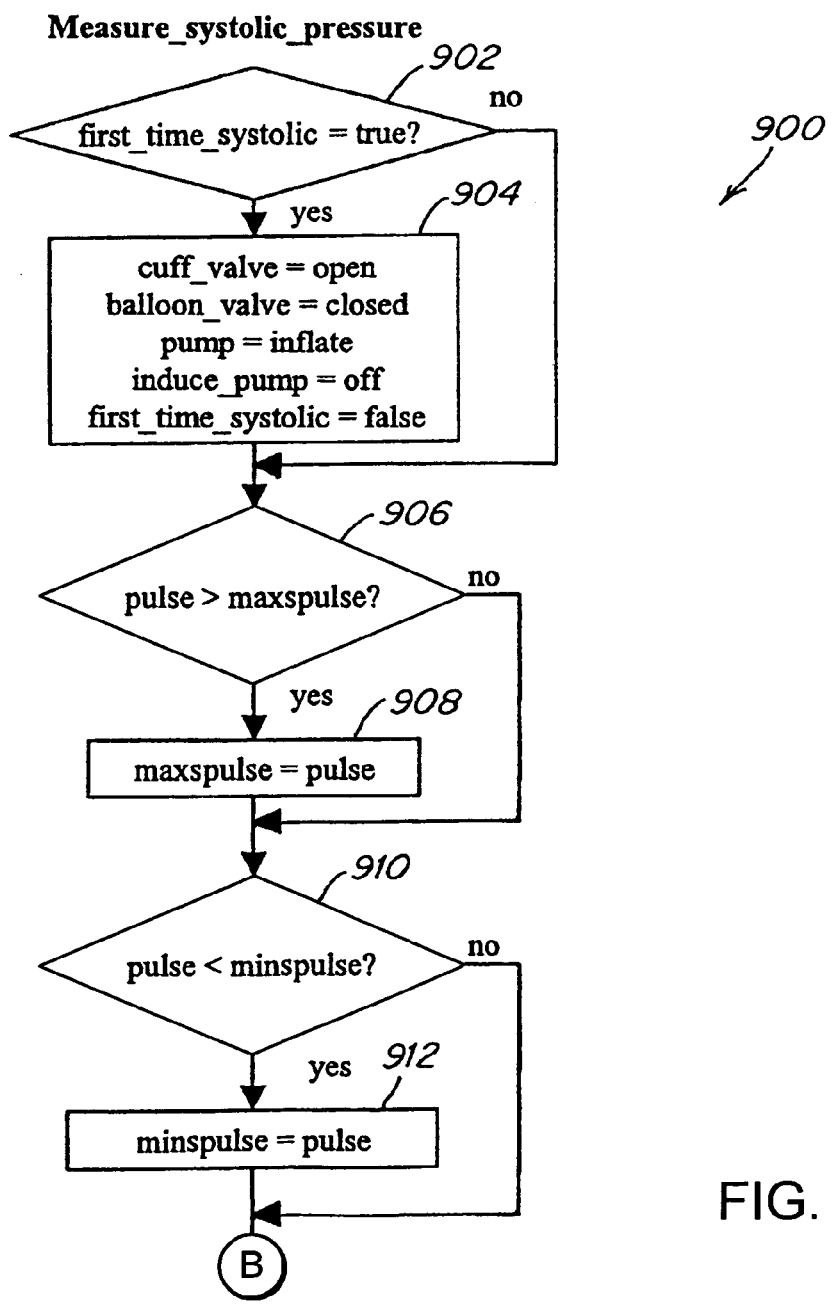
Figures 2, 14P:
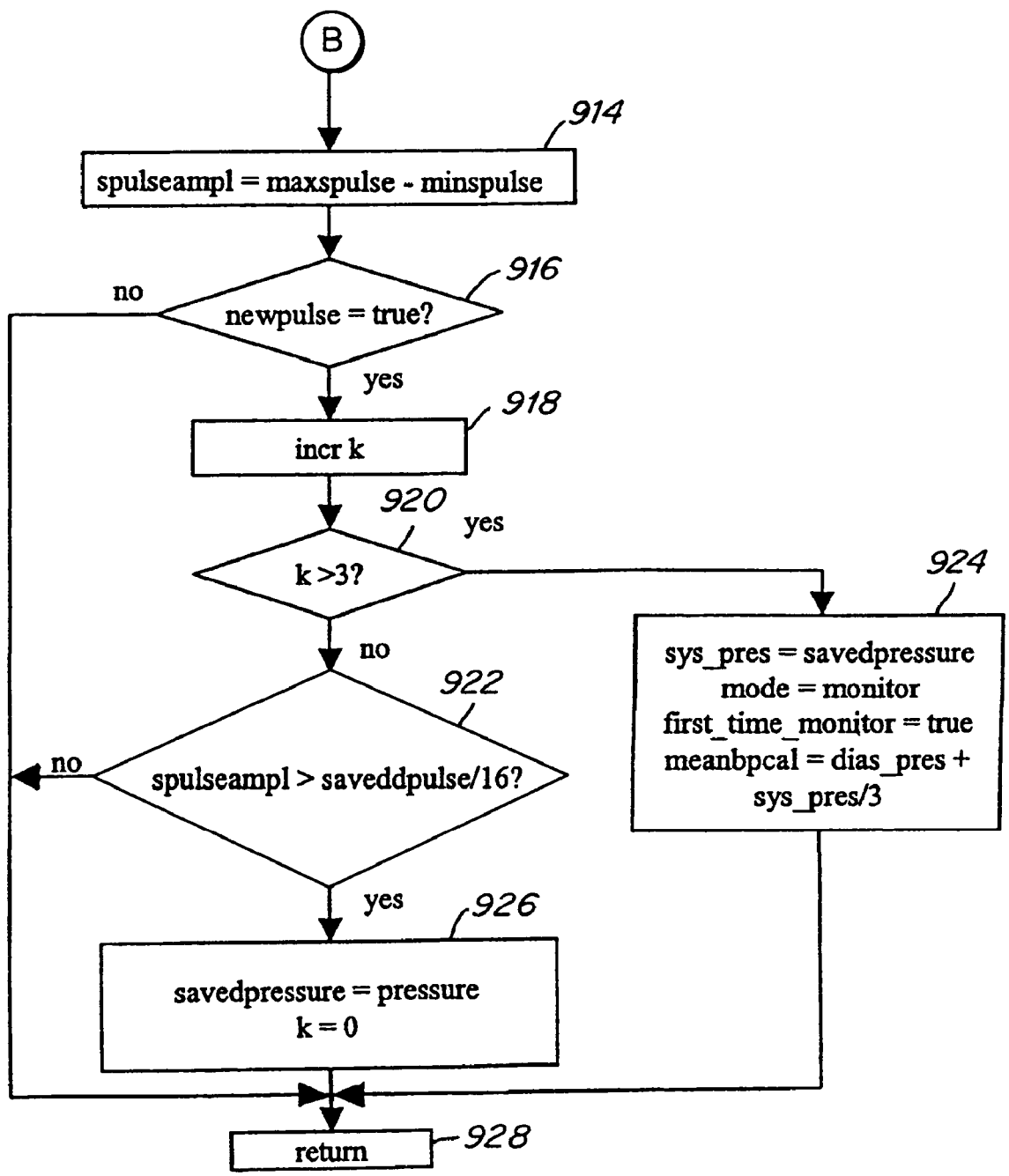

The measure_systolic_pressure subroutine as described in FIG. 14P sets and controls the pneumatics to measure systolic blood pressure by occlusion (cuff valve open, balloon valve closed, induced pressure pump off, pump inflating cuff). It looks for the heart pulse signal disappearing, saves the pressure when the pulse signal disappears, and outputs the pressure as systolic BP.

The readout_results subroutine as described in FIG. 14N takes the most recent values of pulse rate, systolic BP, and diastolic BP and displays them as numeric values on the front panel display. It also updates the trend display, if selected, with the most current data values.

The increment_timer subroutine as described in FIG. 14C increments the timer count.

The continuous_monitor subroutine as described in FIG. 14D sets the pneumatics for continuous BP monitoring (cuff valve open, balloon valve open, induced pressure pump on, pump at initially 40 mmHg or as required). It sets the initial mean blood pressure monitoring signal (meanbpsig0) at the product of initial values for average induced pulse amplitude (ipulseavg) and average dc photocell voltage (dcpcellavg).

The compute_induced_pressure subroutine as described in FIG. 14G computes the peak-to-peak value of the induced pressure signal (ipress), and computes the average of the signal (ipressavg).

The compute_induced_pulse subroutine as described in FIG. 14E computes the amplitude of the induced pulse signal (ipulse=maxind0−minind0), and computes the average value (ipulseavg).

The compute_heart_pulse subroutine as described in FIG. 14F computes the amplitude of the heart pulse signal (maxpulse0−minpulse0), and then computes the average value (hpulseavg).

Per the compute_pulse_pressure subroutine, as described in FIG. 14H, pulse pressure is computed as the ratio of the heart pulse amplitude to the induced pulse amplitude times the induced pressure amplitude (ipressavg*hpulseavg/ipulseavg). After occlusive measurement of systolic and diastolic BP, a calibration factor for pulse pressure (ppcal) is calculated as the ratio of pulse pressure by occlusion divided by pulse pressure by induced pressure. Thereafter pulse pressure by induced pressure is corrected by multiplying by the calibration factor.

The compute_dc_photocell subroutine as described in FIG. 14I, averages the dc photocell voltage.

The compute_mean_pressure subroutine as described in FIG. 14J, continually revises the static cuff pressure up or down to drive the finger mean blood pressure (arterial mean pressure minus external cuff/balloon pressure) back to the value measured during the occlusive measurement mode. The mean blood pressure signal (meanbpsig) is computed as the product of the induced pulse amplitude (ipulseavg) and the dc photocell voltage (dcpcellavg). If the mean arterial pressure increases, these values will decrease, their product decreases, and the executable instructions will increase the cuff pressure. This decreases the effective mean BP of the finger until it is back to its initial value. The reverse occurs if mean arterial BP decreases.

Per the compute_systolic/diastolic_pressure subroutine, as described in FIG. 14K, continuous systolic blood pressure is computed as mean BP plus two-thirds pulse pressure. Continuous diastolic BP is computed as mean BP minus one-third pulse pressure.

Per the test_result subroutine, as described in FIG. 14M, if systolic BP, diastolic BP or pulse rate change by nominally more than 25%, recalibration is initiated by scheduling occlusive BP measurement.

The read_keys subroutine as described in FIG. 14L reads the state of the pushbutton keys. If the start key or the calibrate key is pressed, the mode is changed to calibrate to take an occlusive measurement and calibrate the monitor. If the stop key is pressed, the mode is changed to wait and measurements are suspended.

The apparatus and system for measuring blood pressure and providing continuous information of the blood pressure is light-weight, having a weight of less than 11 pounds, preferably 10 pounds. This provides for a portable system that can be readily transported by a user.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the diagrams. While various elements of the embodiments have been described as being implemented in software, other embodiments in hardware of firmware implementations may alternatively be used, and vice-versa.

It will be apparent to those of ordinary skill in the art that methods involved in the non-invasive blood pressure monitoring device may be embodied in a computer program product that includes a computer usable medium. For example, such a computer usable medium can include a readable memory device, such as a hard drive device, a CD-ROM, a DVD-ROM, or a computer diskette, having computer readable program code segments stored thereon. The computer readable medium can also include a communications or transmission medium, such as, a bus or a communications link, either optical, wired, or wireless having program code segments carried thereon as digital or analog data signals.

Other aspects, modifications, and embodiments are within the scope of the following claims.

What is claimed is:

1. A method for providing a non-invasive measurement of blood pressure, the method comprising the steps of:
    obtaining a first input signal and a second input signal indicative of occlusive measurements of systolic blood pressure and diastolic blood pressure, respectively;
    tracking a signal indicative of pulse pressure;
    continuously measuring a third signal indicative of mean blood pressure; and
    processing said signals to obtain a measurement indicative of systolic and diastolic blood pressure, wherein at least a portion of the measurement indicative of systolic and diastolic blood pressure is continuous wherein obtaining the second input signal indicative of diastolic blood pressure comprises analyzing the second input signal to identify a maximum amplitude of the signal, the maximum amplitude being indicative of the diastolic blood pressure measurement.

2. The method of claim 1, wherein the first input signal and the second input signal are obtained from a photo-plethysmograph.

3. The method of claim 2, wherein the photo-plethysmograph comprises a light source and a detector.

4. The method of claim 3, wherein the light source is a light emitting diode, a laser or an incandescent lamp.

5. The method of claim 3, wherein the detector is one of a photocell or a photo-resistive device.

6. The method of claim 1, wherein tracking a signal indicative of pulse pressure, pulse pressure characterized as the difference between a systolic pressure measurement and a diastolic pressure measurement, further comprises:
    inducing a pulse signal into a region of interest, and
    obtaining a resultant signal indicative of a combination of the induced pulse signal and a heart pulse signal.

7. The method of claim 6, wherein processing the resultant signal further comprises amplifying the resultant signal, separating the induced pulse signal from the heart pulse signal and calculating the pulse pressure from the relative amplitudes of the induced pulse signal and the heart pulse signal.

8. The method of claim 6, further comprising minimizing a venous response to the induced pulse signal.

9. The method of claim 8, wherein minimizing the venous response comprises at least one of selecting an appropriate frequency for the induced pulse signal and/or applying a constant pressure to the region of interest.

10. A method for providing a non-invasive measurement of blood pressure, the method comprising the steps of:
    obtaining a first input signal and a second input signal indicative of occlusive measurements of systolic blood pressure and diastolic blood pressure, respectively;
    tracking a signal indicative of pulse pressure;
    continuously measuring a third signal indicative of mean blood pressure; and
    processing said signals to obtain a measurement indicative of systolic and diastolic blood pressure, wherein at least a portion of the measurement indicative of systolic and diastolic blood pressure is continuous wherein the step of continuously measuring mean blood pressure further comprises continuously monitoring a voltage signal of a photo-plethysmograph and an amplitude signal of an induced pulse signal.

11. The method of claim 10, wherein the amplitude of the induced pulse signal is proportional to a compliance characteristic of an arterial vasculature.

12. The method of claim 10, further comprising:
    calculating a function of the voltage signal and the amplitude signal, wherein the function is proportional to the mean blood pressure.

13. The method of claim 12, wherein the function is a geometric mean of the voltage signal and the amplitude signal.

14. The method of claim 12, further comprising determining a continuous measurement indicative of systolic blood pressure from the relationship defined by mean blood pressure added to a fraction of the pulse pressure.

15. The method of claim 14, wherein the fraction of the pulse pressure is two-thirds.

16. The method of claim 12, further comprising determining a continuous measurement indicative of diastolic blood pressure from the relationship governed by a fraction of the pulse pressure subtracted from mean blood pressure.

17. The method of claim 16, wherein the fraction of pulse pressure is one-third.

18. A method for providing a non-invasive measurement of blood pressure, the method comprising the steps of:
    obtaining a first input signal and a second input signal indicative of occlusive measurements of systolic blood pressure and diastolic blood pressure, respectively;
    tracking a signal indicative of pulse pressure;
    continuously measuring a third signal indicative of mean blood pressure; and
    processing said signals to obtain a measurement indicative of systolic and diastolic blood pressure, wherein at least a portion of the measurement indicative of systolic and diastolic blood pressure is continuous wherein obtaining the second input signal indicative of diastolic blood pressure comprises analyzing the second input signal to identify a maximum amplitude of the signal, the maximum amplitude being indicative of the diastolic blood pressure measurement, the method further comprises obtaining a new first input signal and a new second input signal and processing the first new input signal and the second new input signal to obtain a new measurement indicative of systolic and diastolic pressure.

* * * * *

UNITED STATES PATENT AND TRADEMARK OFFICE
CERTIFICATE OF CORRECTION

PATENT NO. : 7,601,123 B2
APPLICATION NO. : 10/922826
DATED : October 13, 2009
INVENTOR(S) : Tweed et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1392 days.

Signed and Sealed this

Fifth Day of October, 2010

David J. Kappos
*Director of the United States Patent and Trademark Office*